United States Patent
Ueno et al.

(10) Patent No.: US 9,561,478 B2
(45) Date of Patent: Feb. 7, 2017

(54) SEPARATION MEMBRANE, METHOD OF PRODUCING THE SAME AND SEPARATION MEMBRANE MODULE USING THE SEPARATION MEMBRANE

(71) Applicant: TORAY INDUSTRIES, INC., Tokyo (JP)

(72) Inventors: Yoshiyuki Ueno, Otsu (JP); Masaki Fujita, Otsu (JP); Hiroyuki Sugaya, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 272 days.

(21) Appl. No.: 14/077,850

(22) Filed: Nov. 12, 2013

(65) Prior Publication Data

US 2014/0061121 A1   Mar. 6, 2014

Related U.S. Application Data

(63) Continuation of application No. 12/935,414, filed as application No. PCT/JP2009/056448 on Mar. 30, 2009, now Pat. No. 8,613,361.

(30) Foreign Application Priority Data

Mar. 31, 2008  (JP) .................................. 2008-089943
Mar. 31, 2008  (JP) .................................. 2008-089944

(51) Int. Cl.
*B01D 39/00* (2006.01)
*B01D 39/14* (2006.01)
(Continued)

(52) U.S. Cl.
CPC .............. *B01D 71/48* (2013.01); *B01D 63/02* (2013.01); *B01D 67/0093* (2013.01);
(Continued)

(58) Field of Classification Search
CPC ..... B01D 69/08; B01D 71/68; B01D 2325/36; B01D 69/12; B01D 2053/223; B01D 2239/0654; B01D 2323/02
(Continued)

(56) References Cited

U.S. PATENT DOCUMENTS 4,305,823 A   12/1981  Batzer et al.
4,720,343 A   1/1988   Walch et al.
(Continued)

FOREIGN PATENT DOCUMENTS

EP    0274387    7/1988
EP    1254697    11/2002
(Continued)

OTHER PUBLICATIONS

International Search Report dated Jun. 23, 2009, application No. PCT/JP2009/056448.
(Continued)

*Primary Examiner* — Ana Fortuna
(74) *Attorney, Agent, or Firm* — Ratnerprestia

(57) ABSTRACT

A separation membrane includes a membrane comprising a polymer, characterized in that a functional layer is formed on the surface in one side of the membrane, the peak area percentage of carbon derived from ester group measured by the electron spectroscopy for chemical analysis (ESCA) on the surface of the preceding functional layer is 0.1% (by atomic number) or more but not more than 10 (% by atomic number), and the peak area percentage of carbon derived from ester group measured by the electron spectroscopy for chemical analysis (ESCA) on the surface opposite to the functional layer is not more than 10 (% by atomic number). A separation membrane module suffering from little sticking of organic matters, proteins, platelets and so on is provided with the separation membrane as a built-in membrane.

11 Claims, 2 Drawing Sheets

(51) Int. Cl.

| | |
|---|---|
| B01D 33/21 | (2006.01) |
| B01D 67/00 | (2006.01) |
| B29C 44/04 | (2006.01) |
| B01D 71/48 | (2006.01) |
| B01D 63/02 | (2006.01) |
| B01D 69/02 | (2006.01) |
| B01D 71/38 | (2006.01) |
| B01D 71/40 | (2006.01) |
| B01D 71/44 | (2006.01) |
| B01D 71/68 | (2006.01) |
| B01D 69/08 | (2006.01) |
| A61M 1/16 | (2006.01) |

(52) U.S. Cl.
CPC .......... *B01D 69/02* (2013.01); *B01D 69/087* (2013.01); *B01D 71/38* (2013.01); *B01D 71/40* (2013.01); *B01D 71/44* (2013.01); *B01D 71/68* (2013.01); *A61M 1/16* (2013.01); *B01D 2323/02* (2013.01); *B01D 2323/385* (2013.01); *B01D 2325/36* (2013.01); *B01D 2325/38* (2013.01)

(58) Field of Classification Search
USPC .... 210/490, 500.36, 500.41, 500.42, 500.23, 210/500.27, 500.35, 645, 321, 8; 264/48; 427/244
See application file for complete search history.

(56) References Cited

U.S. PATENT DOCUMENTS

| | | | | |
|---|---|---|---|---|
| 5,294,346 | A | * | 3/1994 | Donato et al. ................ 210/645 |
| 5,340,480 | A | * | 8/1994 | Kawata .............. B01D 67/0011 210/500.23 |
| 7,470,368 | B2 | | 12/2008 | Sugaya et al. |
| 7,868,087 | B2 | | 1/2011 | Mayes et al. |
| 8,070,964 | B2 | * | 12/2011 | Araki et al. ............ 210/748.01 |
| 8,613,361 | B2 | * | 12/2013 | Ueno et al. ................... 210/490 |
| 9,023,947 | B2 | * | 5/2015 | Tomita et al. ................ 525/153 |
| 2004/0247682 | A1 | | 12/2004 | Sugaya et al. |
| 2005/0273031 | A1 | | 12/2005 | Ueno et al. |
| 2006/0108288 | A1 | * | 5/2006 | Oishi ............................ 210/639 |
| 2007/0114167 | A1 | * | 5/2007 | Mabuchi et al. ........ 210/321.89 |
| 2011/0017654 | A1 | * | 1/2011 | Ueno et al. ................ 210/321.6 |
| 2011/0210064 | A1 | | 9/2011 | Cheng et al. |
| 2013/0306544 | A1 | * | 11/2013 | Ueno et al. .............. 210/321.79 |

FOREIGN PATENT DOCUMENTS

| | | |
|---|---|---|
| GB | 2035133 | 6/1980 |
| JP | 62-014903 A | 1/1987 |
| JP | 62-163703 | 7/1987 |
| JP | 62-197105 A | 8/1987 |
| JP | 08-9668 | 4/1988 |
| JP | 2-18695 | 4/1990 |
| JP | 04-094727 A | 3/1992 |
| JP | 06-165926 A | 6/1994 |
| JP | 06-238139 | 8/1994 |
| JP | 07-011019 A | 1/1995 |
| JP | 08-131791 | 5/1996 |
| JP | 08131793 | 5/1996 |
| JP | 10-099666 A | 4/1998 |
| JP | 2002-370021 A | 12/2002 |
| JP | 2006-198611 | 8/2006 |
| JP | 2006-231333 A | 9/2006 |
| WO | WO2004018085 A1 | 3/2004 |
| WO | WO 2006/104117 | 10/2006 |

OTHER PUBLICATIONS

"Nano Bioengineering: Fusion of Advanced Medicine and Nanotechnology," Kazunori Kataoka, pp. 115-116, Oct. 15, 2007 (with partial translation).
Extended European Search Report dated Aug. 18, 2015 for European Application No. 09727576.2.

* cited by examiner

SEPARATION MEMBRANE, METHOD OF PRODUCING THE SAME AND SEPARATION MEMBRANE MODULE USING THE SEPARATION MEMBRANE

CROSS REFERENCE TO RELATED APPLICATIONS

This application is a Continuation application of U.S. application Ser. No. 12/935,414, filed Sep. 29, 2010, which is the U.S. National Phase application of PCT International Application No. PCT/JP2009/056448, filed Mar. 30, 2009, and claims priority of Japanese Patent Application Nos. 2008-089943, filed Mar. 31, 2008, and 2008-089944, filed Mar. 31, 2008, the disclosures of each of the foregoing applications being incorporated herein by reference in their entireties for all purposes.

FIELD OF THE INVENTION

The invention relates to a separation membrane and a separation membrane module, which have high separation performance and are suitable for use in applications where compatibility with blood and resistance to the deposition of proteins or organic substances are required. For example, separation membranes for use in blood purification are required to have compatibility with blood and resistance to the deposition of proteins, and water purifier membranes, water purification membranes, waste water clarification membranes, reverse osmosis membranes, membranes for separating biological components, and so on are required to have resistance to the deposition of proteins or organic substances. Therefore, the separation membrane and the separation membrane module according to the invention are preferably used in these fields.

BACKGROUND OF THE INVENTION

When proteins or blood platelets are deposited on a medial separation membrane in contact with body fluid or blood, they can cause a reduction in the performance of the separation membrane or a biological reaction, which raises a serious problem. Also when a water treatment membrane is used in a water purifier or the like, the deposition of proteins or organic substances causes a reduction in the performance of the separation membrane. In attempts to solve these problems, various studies have been made by hydrophilizing separation membranes. For example, there are disclosed methods that include mixing polyvinylpyrrolidone, a hydrophilic polymer, with polysulfone in the step of preparing a membrane forming stock solution and then subjecting the stock solution to a membrane-forming process so that a membrane having hydrophilicity and prevented from being fouled can be produced (Patent Document 1). However, these methods have certain limitations such as the need for a large amount of a hydrophilic polymer in the membrane forming stock solution for imparting hydrophilicity to the surface, the need to limit the hydrophilic polymer to one with compatibility with the base polymer, and the need to examine the optimal stock solution composition depending on the intended use of the material.

Patent Document 2 discloses a method of hydrophilizing a membrane by coating the membrane with polyvinyl acetal diethylamino acetate and a hydrophilizing agent. In this method, the hydrophilizing agent is covered with polyvinyl acetal diethylamino acetate, so that the deposition resistance effect may be drastically reduced. In addition, when the membrane is immersed in each of a polyvinyl acetal diethylamino acetate solution and a hydrophilizing solution, the separation performance of the membrane may be reduced.

There are also disclosed a method that includes making a hydrophilic component such as polyvinylpyrrolidone water-insoluble by radiation or heat so that the hydrophilic component can be introduced into a membrane being produced (Patent Document 3) and a method that includes bringing a polysulfone-based separation membrane into contact with a solution of a hydrophilic polymer such as polyvinylpyrrolidone and then forming an insolubilized coating layer by radiation crosslinking (Patent Document 4). However, there is a problem in which the intermolecular interaction between the aqueous polymer such as polyvinylpyrrolidone and the polysulfone-based polymer is weak, so that the coating layer is difficult to form.

Thus, there is disclosed a method that includes bringing an aqueous solution of a polyvinyl alcohol with a saponification degree in a certain range into contact with a polysulfone-based separation membrane so that a coating layer can be efficiently formed on the membrane surface by hydrophobic interaction between polysulfone and vinyl acetate (Patent Document 5). As a result of studies by the inventors, it has been found that when a separation membrane is simply coated with polyvinyl alcohol according to the publication, the performance of the separation membrane is significantly reduced, because the method disclosed in the publication does not relate to the deposition resistance. It is also known that the hydroxyl group of polyvinyl alcohol tends to activate complements, when brought into contact with blood.

It is also said that even when a material surface is coated with a hydrophilic polymer such as polyvinylpyrrolidone or polyethylene glycol, the deposition of proteins and so on can be only temporarily inhibited (Non-Patent Document 1). Under the circumstances, a separation membrane module having a high-performance membrane and satisfactory compatibility with blood has not yet been established.

Patent Document 1: Japanese Patent Application Publication (JP-B) No. 02-18695
Patent Document 2: Japanese Patent Application Laid-Open (JP-A) No. 08-131791
Patent Document 3: JP-B No. 08-9668
Patent Document 4: JP-A No. 06-238139
Patent Document 5: JP-A No. 2006-198611
Non-Patent Document 1: Iryo Nanotechnology (Medical Nanotechnology), Kyorin-Tosho, pp. 115-116

SUMMARY OF THE INVENTION

The invention provides a high-performance separation membrane module that resists deposition of proteins or organic substances.

As a result of intensive studies, the inventors have found that the separation membrane and the separation membrane module according to aspects of the invention, which have high compatibility with blood and resist deposition of proteins or organic substances, are achieved by the feature recited in any one of items 1 to 15 below.

1. A separation membrane, comprising a membrane comprising a polymer, wherein the membrane has a functional layer in one side surface, the functional layer has a surface showing an ester carbon peak area percentage of 0.1 (at. % (atomic percent)) to 10 (at. %) as measured by X-ray electron spectroscopy (ESCA), the membrane has an opposite surface from the functional layer, and the opposite surface shows an ester carbon peak area percentage of 10 (at. %) or less as measured by X-ray electron spectroscopy (ESCA).

2. The separation membrane, wherein the surface of the functional layer has an ester carbon content higher than that of the opposite surface from the functional layer.

3. The separation membrane according to item 1 or 2, wherein the ester is derived from an ester group-containing polymer.

4. The separation membrane according to any one of items 1 to 3, wherein the membrane contains a hydrophobic polymer.

5. The separation membrane according to item 4, wherein the hydrophobic polymer is a polysulfone-based polymer.

6. The separation membrane according to any one of items 1 to 5, which is a hollow fiber membrane.

7. The separation membrane according to any one of items 1 to 6, wherein the membrane contains a water-soluble polymer having a solubility of 1 g or more in 100 g of water at 20° C.

8. The separation membrane according to item 3, wherein the ester group-containing polymer has at least one selected from a vinyl carboxylate ester unit, an acrylate ester unit and a methacrylate ester unit.

9. The separation membrane according to item 3 or 8, wherein the ester group-containing polymer is polyvinyl acetate or a copolymer of vinyl acetate and vinylpyrrolidone.

10. The separation membrane according to any one of items 1 to 9, which is for use in blood purification.

11. A separation membrane module, comprising the separation membrane according to any one of items 1 to 10 as a built-in element.

12. A method of producing a separation membrane containing a hydrophobic polymer, comprising the step of forming a coating of an ester group-containing polymer, wherein the ester group-containing polymer has an adsorption equilibrium constant of 330 pg/(mm$^2$·ppm) to 1,100 pg/(mm$^2$·ppm) on the hydrophobic polymer, and a solution of the ester group-containing polymer is brought into contact with the hydrophobic polymer under a pressure difference generated between the inside and the outside of the separation membrane.

13. The method according to item 12, wherein the step of forming the coating comprises bringing the solution of the ester group-containing polymer into contact with the separation membrane and performing irradiation with radiation and/or heat treatment.

14. A separation membrane for use in blood purification, comprising the separation membrane produced by the method according to item 12 or 13.

15. A separation membrane module, comprising, as a built-in element, the separation membrane produced by the method according to any one of items 12 to 14.

The separation membrane and the separation membrane module are characterized in that ester groups are localized at the surface of the functional layer of the separation membrane, so that they have high separation performance and can be widely used in applications where compatibility with blood and resistance to the deposition of proteins or organic substances are required.

DESCRIPTION OF REFERENCE CHARACTERS

Figure 1:
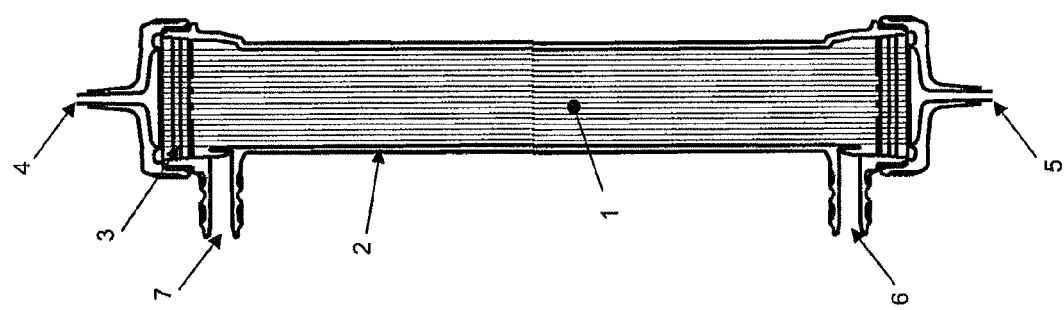
FIG. 1 illustrates an artificial kidney for use in an embodiment of the invention.

In the drawings, reference numeral 1 represents a hollow fiber membrane, 2 a case, 3 a potting agent, 4 a blood side inlet (Bi), 5 a blood side outlet 1 (Do), 6 a dialyzate side inlet (Di), 7 a dialyzate side outlet (Do), 8 a base line, 9 a dialyzer, 10 a hollow fiber membrane module, 11 a Bi pump, 12 an F pump, 13 a waste container, 14 blood for circulation, 15 blood for clearance measurement, 16 a Bi circuit, 17 a Bo circuit, 18 a Di circuit, 19 a Do circuit, and 20 a warm water tank.

DETAILED DESCRIPTION OF THE INVENTION

The separation membrane is characterized by having a functional layer in one side surface of the membrane and having ester groups localized at the surface of the functional layer.

The ester groups present at the surface of the functional layer in the separation membrane inhibit deposition of proteins or blood platelets. Deposition of proteins on material surfaces is said to be due to the fact that as the higher order structure of proteins changes, their hydrophobic sites are exposed from the inside to cause hydrophobic interaction with the material surfaces. On the other hand, water whose mobility is constrained by hydrogen bonding, so-called bound water, is present around proteins or on material surfaces. Therefore, the interaction between bound water each other is important for the deposition of proteins on material surfaces. Thus, it is said that deposition of proteins on material surfaces having strong hydrophilicity cannot be sufficiently suppressed, because bound water around the proteins are also trapped by such surfaces. The mechanism of the protein deposition-inhibiting effect of the ester groups is not sufficiently clear. Considering the above, however, it is speculated that since the ester groups are hydrophilic, they may not induce a change in the higher order structure of proteins and that since the degree of the hydrophilicity is not so high, they may also not trap bound water around proteins.

As described above, it is preferred to localize ester groups at the surface of the functional layer in the separation membrane, and therefore, the surface of the functional layer shows an ester carbon peak area percentage of 0.1 (at. % (atomic percent)) or more, preferably 0.5 (at. %) or more, more preferably 1 (at. %) or more as measured by X-ray electron spectroscopy (hereinafter also referred to as ESCA). If the number of ester groups is too large, a reduction in the performance of the separation membrane may be observed. Thus, it is preferably 10 (at. %) or less, more preferably 5 (at. %) or less.

If a large number of ester groups are present at the opposite surface from the functional layer, the performance of the separation membrane will be reduced. Therefore, the opposite surface from the functional layer shows an ester carbon peak area percentage of 10 (at. %) or less, preferably 5 (at. %) or less, more preferably 1 (at. %) or less as measured by X-ray electron spectroscopy (ESCA).

Deposition of proteins and so on only have to be suppressed at the surface of the functional layer, and therefore, the ester carbon content is preferably higher at the surface of the functional layer than at the opposite surface from the functional layer, so that the separation performance can be higher. In this case, the ester carbon content of the surface of the functional layer should be 10% or more, preferably 15% or more, more preferably 20% or more, even more preferably 30% or more higher than that of the opposite surface.

The ester carbon at the surface may be quantified by X-ray electron spectroscopy (ESCA). Values measured at an angle of 90° should be used. At a measurement angle of 90°, a region from the surface to a depth of about 10 nm can be detected. The average of values measured at three places should be used. The ester (COO) carbon peak may be determined by deconvoluting peaks observed in the range from the main C1s peak derived from CH or C—C to the peak at +4.0 to +4.2 eV higher. The ester carbon content (at. %) is determined by calculating the ratio of the corresponding peak area to the peak area for all elements. More specifically, C1s peaks are composed of five components: a component mainly derived from CHx, C—C, C=C, C—S; a component mainly derived from C—O, C—N; a component derived from π-π* satellite; a component derived from C=O; and a component derived from COO. Therefore, the peaks are deconvoluted into the five components. The COO-derived component corresponds to the peak observed at an energy +4.0 to +4.2 eV higher than the main CHx or C—C peak (at about 285 eV). When calculated, the first decimal place of the peak area ratio of each component is rounded off. The ester carbon content may be calculated by multiplying the C1s carbon content (at. %) by the peak area ratio of the COO-derived component. As a result of peak deconvolution, a ratio of 0.4% or less is determined to be the detection limit or less.

As used herein, the term "the surface of the functional layer (the functional layer surface)" refers to the surface on the side to be in contact with materials to be treated or liquids to be treated in the case of liquid treatment. For example, in the case of a hollow fiber membrane for artificial kidney, the inner surface corresponds to the surface of the functional layer through which blood (the liquid to be treated) flows, and the outer surface corresponds to the opposite surface through which the dialyzate solution flows.

After the separation membrane is formed, the surface of the functional layer may be chemically modified with an ester group-containing reactive compound, so that ester groups can be introduced onto the surface of the functional layer. However, such a surface reaction may cause a reduction in the performance of the separation membrane, and there are various condition limits to actual use of such a surface reaction.

Therefore, an ester group-containing polymer should be used so that polymer-derived ester groups can be relatively easily introduced onto the surface of the functional layer. Examples of such an ester group-containing polymer include a polymer of lactic acid, polyester or the like, the main chain of which contains ester groups; a polymer made from a monomer containing an ester group in the side chain, such as a vinyl carboxylate ester such as vinyl acetate, an acrylate ester such as methyl acrylate or methoxyethyl acrylate, an methacrylate ester such as methyl methacrylate, ethyl methacrylate or hydroxyethyl methacrylate; and vinyl acetate. In an embodiment of the invention, an aromatic ring-containing polymer such as polyethylene terephthalate may have a too high hydrophobicity and therefore is not preferably used as the ester group-containing polymer. To improve the function of inhibiting the deposition of proteins or blood platelets, a polymer having an ester group-containing side chain, such as a polymer of a vinyl carboxylate ester, an acrylate ester or a methacrylate ester is preferred. In particular, vinyl acetate is highly effective in inhibiting the deposition of proteins or blood platelets.

The localization of the ester group-containing polymer at the surface of the functional layer in the separation membrane is also preferred to improve the membrane performance. This may be because if the ester group-containing polymer is not localized at the surface and also exists in a large amount in the thickness direction, water molecules may be constrained by hydrogen bonding or other effects, so that the membrane may be less permeable to water molecules in blood or waste products or other products dissolved therein.

Thus, the content of the ester group-containing polymer in the surface of the functional layer of the membrane is preferably 30% or more, more preferably 100% or more, even more preferably 300% or more higher than the content of the ester group-containing polymer in the inside of the membrane.

Whether the content of the ester group-containing polymer in the membrane surface is higher than that in the inside of the membrane may be typically determined by a combination of ESCA and total reflection infrared spectroscopy (hereinafter also referred to as ATR). This is because ESCA can measure a region from the surface to a depth of about 10 nm, and ATR can measure the composition up to a depth of several μm, although it measures the surface. For example, in the case of a polysulfone separation membrane, the ratio of the content of the ester group-containing polymer to the content of the polysulfone unit at any place in the membrane may be determined as a unit content ratio. If the unit content ratio obtained by ESCA is 30% or more higher than that obtained by ATR, it may be determined that the content of the ester group-containing polymer in the membrane surface is 30% or more higher than that in the inside of the membrane. Each measured value should be the average of measurements at three points.

For example, the method described below may be used to localize the ester group-containing polymer at the surface of the functional layer in the separation membrane. In a process of producing a membrane from a membrane forming stock solution by a wet method, a higher molecular weight polymer tends to gather at the surface so that entropy loss can be prevented, and a hydrophilic polymer tends to gather at the surface so that enthalpy loss can be prevented. For example, therefore, in the case of a polysulfone membrane, a stock solution comprising three polymer components: polysulfone; polyvinylpyrrolidone; and the ester group-containing polymer may be prepared, and the molecular weight of the ester group-containing polymer may be set equal to or more than that of polyvinylpyrrolidone, so that the ester group-containing polymer can be concentrated at the surface. However, if the ester group-containing polymer has a high affinity for polysulfone, the enthalpy effect may be dominant over the entropy effect, so that the ester groups can be concentrated in the inside of the separation membrane rather than in the surface. In general, a copolymer of an ester group unit and another unit such as a vinylpyrrolidone unit, which would otherwise exhibit water solubility in a homopolymer, is preferably used rather than a homopolymer comprising only an ester group unit, because such a copolymer has a low affinity for polysulfone. When the separation membrane is a hollow fiber membrane, the ester group-containing polymer may be added to an injection liquid which is allowed to flow in the inside in the process of discharge from a double-annular nozzle. Before the hollow fiber membrane undergoes phase separation so that the membrane structure is established, the ester group-containing polymer diffuses from the injection liquid to the membrane forming stock solution side, so that it can be localized at the inner surface. After the production of a hollow fiber membrane, a method of coating the functional layer surface of the separation membrane with the ester group-containing polymer may also be conveniently and preferably used. Alternatively, the ester group-containing polymer may be fixed on a hollow fiber membrane by a chemical reaction therebetween. After the coating, crosslinking the separation membrane by radiation or heat treatment is a preferred method for preventing the elution of the ester group-containing polymer.

In an embodiment of the invention, a hydrophobic polymer is preferably used as a base material for the separation membrane. As used herein, the term "hydrophobic polymer" refers to a polymer having a solubility of less than 0.001 g in 100 g of water at 20° C. Examples of hydrophobic polymers include, but are not limited to, polysulfone-based polymers, polystyrene, polyurethane, polyethylene, polypropylene, polycarbonate, polyvinylidene fluoride, and polyacrylonitrile. In particular, polysulfone-based polymers are preferably used, because they can easily form a separation membrane and be easily coated with the ester group-containing polymer. As used herein, the term "polysulfone-based polymers" refers to polymers having an aromatic ring, a sulfonyl group and an ether group in the main chain, examples of which include polysulfone, polyethersulfone, and polyarylethersulfone. For example, a polysulfone represented by formula (1) or (2) below is preferably used as a non-limiting example in an embodiment of the invention. In each formula, n is typically an integer of 50 to 80.

layer in the separation membrane. Thus, the inventors have contemplated that an index of such an ester group content can be expressed by a ratio obtained by dividing the ester group content by the polysulfone content. As a result of investigations, it has been found that if the ratio $(A_{CO})/(A_{CC})$ of the intensity $(A_{CO})$ of an infrared absorption peak derived from ester group C=O at about 1730 cm$^{-1}$ to the intensity $(A_{CC})$ of an infrared absorption peak derived from polysulfone benzene ring C=C at about 1580 cm$^{-1}$ is selected and determined at three different places of the functional layer surface of the separation membrane, the average of the determined ratios should preferably be 0.005 or more, more preferably 0.01 or more, even more preferably 0.02 or more, and the rate of the measurement points at which the ratio is 0.001 or less should preferably be 10% or less, more preferably 5% or less. If the average $(A_{CO})/(A_{CC})$ is too high, the separation membrane performance may be reduced. Therefore, it is preferably 1 or less, more preferably 0.5 or less. The $(A_{CO})/(A_{CC})$ ratio may be calculated as described below. The absorption intensity of the infrared absorption spectrum of the functional layer surface is measured at 25 points in a measurement area of 3 μm×3 μm with a cumulative number of 30 or more. The 25-point measurement is performed at three different places. A base line is drawn on the resulting infrared absorption spectrum in the range of 1,549 to 1,620 cm$^{-1}$, and $A_{CC}$ is defined as the peak area surrounded by the base line and the positive part of the spectrum. Similarly, a base line is drawn on the spectrum in the range of 1,711 to 1,759 cm$^{-1}$, and $A_{CO}$ is defined as the corresponding peak area. The ratio between them $(A_{CO})/(A_{CC})$ is then calculated.

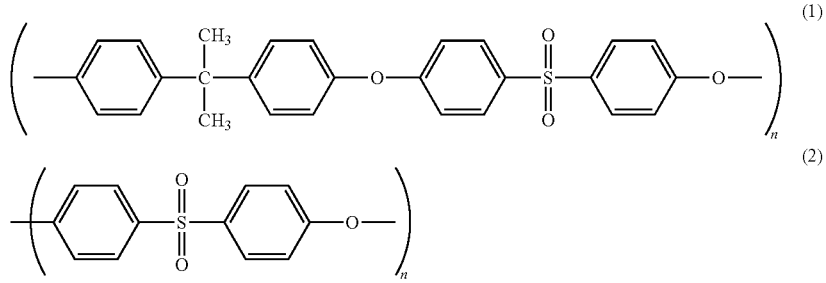

Examples of polysulfone include Udel Polysulfone P-1700 and P-3500 (manufactured by Solvay S.A.), Ultrason S3010 and S6010 (manufactured by BASF), Victrex (Sumitomo Chemical Co., Ltd.), Radel A (manufactured by Solvay S.A.), and Ultrason E (manufactured by BASF). A polymer comprising only a repeating unit represented by formula (1) and/or a repeating unit represented by formula (2) is preferably used as a polysulfone in an embodiment of the invention. On the other hand, such a repeating unit(s) may be copolymerized or modified with any other monomer, as long as the effects of the invention are not impaired. The content of any other copolymerized monomer is preferably, but not limited to, 10% by weight or less.

In general, polysulfone-based polymers are highly hydrophobic, so that a relatively large amount of organic substances such as proteins can be deposited thereon. It has been discovered that when the ester group content is relatively low based on the polysulfone content, activated proteins or platelets are particularly deposited even on the ester group-containing surface, and it has been concluded that at least a certain amount of ester groups are desired to be uniformly present at all parts of the surface of the functional When the separation membrane forms a hollow fiber membrane module including a large number of hollow fiber membranes, the three different places to be measured preferably include both ends and the center of the module. In addition, three or more hollow fibers are preferably measured.

In a method for setting $(A_{CO})$ $(A_{CC})$ in the above range, when the ester group-containing polymer is added to the membrane forming stock solution, it is desirous to adjust conditions such as the component ratios of the membrane forming stock solution, the nozzle temperature during spinning, and the temperature and humidity of the discharge part. These conditions also depend on the type or molecular weight of the ester group-containing polymer. For example, when Kollidon VA64 (BASF), a copolymer of vinylpyrrolidone and vinyl acetate (6/4), is used as the ester group-containing polymer, the VA64 content of the membrane forming stock solution is preferably in the range of 1 to 10% by weight, the nozzle temperature preferably in the range of 20 to 60° C., the dry part temperature preferably in the range of 10 to 60° C., and the relative humidity preferably in the range of 70 to 95% RH. When the ester group-containing polymer is added to the injection liquid, the component ratios of the injection liquid, the injection liquid temperature, the composition of the membrane forming stock solution, or the like has a certain effect. For example, in the case of VA64, the content of VA64 in the injection liquid is preferably in the range of 5 to 30% by weight, the injection liquid temperature preferably in the range of 10 to 60° C., and the polysulfone-based polymer concentration of the membrane forming stock solution composition preferably in the range of 14 to 25% by weight, or alternatively when polyvinylpyrrolidone is used, its concentration is preferably from 2 to 10% by weight. For easy diffusion of VA64 into the membrane, the polysulfone-based polymer to be used preferably has a weight average molecular weight of 100,000 or less, more preferably 50,000 or less. When a polysulfone membrane is subjected to a post-treatment such as coating, the concentration of the ester group-containing polymer in the coating liquid, the contact time, or the coating temperature has a certain effect. For example, when coating with an aqueous VA64 solution is performed, the VA64 concentration is preferably in the range of 1 to 5,000 ppm, the contact time preferably 10 seconds or more, and the temperature preferably in the range of 10 to 80° C. When the coating is performed continuously rather than in a batch mode, it can be uniformly performed at a relatively-high, aqueous VA64 solution, flow rate. However, a too high flow rate may make the coating amount insufficient, and therefore, the flow rate is preferably in the range of 200 to 1,000 mL/minute.

In view of the inhibition of the deposition of proteins or blood platelets, the separation membrane preferably contains a water-soluble polymer having a solubility of 1 g or more, preferably 10 g or more in 100 g of water at 20° C. in addition to the ester group-containing polymer. It has been considered that a good balance between hydrophilicity and hydrophobicity at the surface should be important for the inhibition of the deposition of proteins or blood platelets. In fact, when a water-soluble polymer having higher hydrophilicity than the ester group-containing polymer is present in addition to the ester group-containing polymer, the effect of inhibiting the deposition of proteins or blood platelets is further improved. Such a water-soluble polymer is preferably polyvinylpyrrolidone, polyethylene glycol, or polyvinyl alcohol. The content of the water-soluble polymer in the separation membrane is preferably 0.1% by weight or more, more preferably 1% by weight or more. If the content is too high, the membrane performance may tend to be low. Thus, the content is preferably 30% by weight or less, more preferably 10% by weight or less. The content of the water-soluble polymer in the surface of the functional layer is preferably 10% by weight or more, more preferably 15% by weight or more. Since a too high content may make the hydrophilic effect too high, the content is preferably 50% by weight or less, more preferably 40% by weight or less. The content of the ester group-containing polymer in the separation membrane may be determined by elemental analysis or nuclear magnetic resonance (NMR) measurement. The content of the water-soluble polymer in the functional layer surface may be determined by ESCA or the like.

It is also preferred that the ester group-containing polymer should be a copolymer having a water-soluble unit and an ester group unit, because such a copolymer can achieve a good balance between hydrophilicity and hydrophobicity in a single molecule. In this case, a block copolymer, an alternating copolymer or a random copolymer rather than a graft copolymer is preferably used. This may be because the unit moiety grafted on the main chain of a graft copolymer can frequently contact with proteins, so that the properties of the graft chain moiety can have a higher effect than the properties of the copolymer itself. An alternating copolymer or a random copolymer is more preferred than a block copolymer, because it is considered that the respective units of a block copolymer can have clearly distinctive properties. In view of the balance between hydrophilicity and hydrophobicity in a single molecule, a copolymer comprising at least one selected from a random copolymer and an alternating copolymer is preferably used. In such an ester group-containing polymer, the molar ratio of the ester group unit is preferably from 0.3 to 0.7. If the molar ratio of the ester group unit is less than 0.3, the deposition-inhibiting effect of the ester group may be low. If it is more than 0.7, the effect of the water-soluble unit may be low.

The molar ratios of these units may be determined by NMR, elemental analysis or the like.

Examples of the water-soluble unit include a vinylpyrrolidone group, an ethylene glycol group, a vinyl alcohol group, and so on. In particular, a vinylpyrrolidone-vinyl acetate copolymer has a good balance between hydrophilicity and hydrophobicity and therefore is preferably used. The balance between hydrophilicity and hydrophobicity over the entire surface is also important, and therefore, the content of the vinylpyrrolidone unit in the surface is preferably 10% by weight or more, more preferably 15% by weight or more. Since a too high content may make the hydrophilic effect too high, the content is preferably 50% by weight or less, more preferably 40% by weight or less. When the separation membrane contains polyvinylpyrrolidone as described above, the vinylpyrrolidone unit content of the surface is the sum of the contents of the vinylpyrrolidone units derived from the polyvinylpyrrolidone and the copolymer comprising a vinylpyrrolidone unit and an ester group unit. The vinylpyrrolidone unit content of the surface may be determined by ESCA.

When the water-soluble polymer has good compatibility with the hydrophobic polymer used as a base material for the separation membrane, it may be added to the membrane forming stock solution and preferably used as a pore forming agent. For example, polyvinylpyrrolidone (PVP), polyvinyl alcohol (PVA) or polyethylene glycol (PEG) is preferably used in combination with the polysulfone-based polymer.

As mentioned above, methods that are preferably used for introducing the ester group-containing polymer onto the functional layer surface include a method including mixing the polymer into a membrane forming stock solution and subjecting the stock solution to a membrane forming process, a method of mixing the polymer into an injection liquid, and a method of coating the formed separation membrane with the polymer. A method of performing insolubilization by irradiation or heat treatment after the coating or a method including immersing a separation membrane in a hydrophobic monomer mixture solution and performing a polymerization reaction on the separation membrane surface may also be used.

Among these methods, the method of coating the separation membrane surface with the ester group-containing polymer is particularly preferred, because it can be conveniently performed with a small amount of the polymer. For example, a solution of the ester group-containing polymer in a solvent may be applied and adsorbed to the separation membrane, or the ester group-containing polymer may be fixed on the base material of the separation membrane using an adhesive or a similar material. Alternatively, in the process of bringing the ester group-containing polymer into contact with the separation membrane surface, a pressure difference may be generated between the front (functional layer) and back of the separation membrane and used for the concentration of the polymer at the membrane surface. This method is efficient and therefore preferably used. The pressure difference may be generated by compression or decompression. There is also a method of generating a pressure difference using an ester group-containing polymer solution itself so that the polymer can be introduced onto the membrane surface. Alternatively, after the contact of the solution, gas, water or any other solution may be used for pressurization.

It has been found that particularly in the process of coating the separation membrane surface with the ester group-containing polymer, when the ester group-containing polymer has a higher adsorption equilibrium constant on the hydrophilic polymer used as the base material of the separation membrane, the separation membrane surface can be more uniformly coated. If the size of the ester group-containing polymer is smaller than the pore size of the separation membrane, the ester group-containing polymer can pass through the membrane even under a pressure difference generated between the inside and outside of the separation membrane, so that the ester group-containing polymer cannot be efficiently localized at the functional layer surface. However, it has been found that when the adsorption equilibrium constant is high, the ester group-containing polymer can be efficiently localized at the surface regardless of its molecular weight. Specifically, the adsorption equilibrium constant is preferably 330 pg/(mm$^2$·ppm) or more, more preferably 500 pg/(mm$^2$·ppm) or more, even more preferably 550 pg/(mm$^2$·ppm) or more, particularly preferably 600 pg/(mm$^2$·ppm) or more. On the other hand, if the polymer used has an adsorption equilibrium constant of more than 1,100 pg/(mm$^2$·ppm) on the hydrophobic polymer that forms the separation membrane, an excess amount of the polymer may adsorb upon contact with the separation membrane, which may reduce the size of the membrane pore, so that a reduction in the separation membrane performance, such as a reduction in the protein clearance efficiency may occur. Therefore, the adsorption equilibrium constant is preferably 1,100 pg/(mm$^2$·ppm) or less, more preferably 1,000 pg/(mm$^2$·ppm) or less, even more preferably 900 pg/(mm$^2$·ppm) or less, particularly preferably 850 pg/(mm$^2$·ppm) or less.

It should be noted that if the adsorption equilibrium constant is too high, the amount of adsorption on the membrane may be so large that the performance may be often reduced. However, this problem can be coped with by lowering the concentration of the coating solution or reducing the amount of the coating solution.

The pressure difference between the inside and outside of the separation membrane is preferably 5 kPa or more, more preferably 10 kPa or more, even more preferably 20 kPa or more. Since a too large pressure difference may cause leakage through the separation membrane, the pressure difference is preferably 100 kPa or less, more preferably 70 kPa or less, even more preferably 50 kPa or less. As used herein, the term "the inside of the separation membrane" refers to the surface side of the functional layer of the separation membrane to be in contact with the liquid to be treated, and "the outside" refers to the opposite side therefrom. For example, in the case of a hollow fiber membrane for artificial kidney, the surface of the functional layer through which blood (the liquid to be treated) flows corresponds to the inside, and the opposite surface through which the dialyzate solution flows corresponds to the outside.

In an embodiment of the invention, the adsorption equilibrium constant is a value obtained by measurement with a surface plasmon resonance (hereinafter abbreviated as SPR) analyzer and calculation. The SPR analyzer analyzes changes in the mass of a thin film surface from changes in the resonance angle of a laser beam applied at a constant angle. A thin film of the hydrophobic polymer to be used in the separation membrane is formed on a gold chip for SPR by spin coating. Aqueous solutions of the ester group-containing polymer at concentrations arbitrarily selected from the range of 5 to 1,000 ppm are each allowed to flow on the chip, while each adsorbed amount is measured. The adsorption equilibrium constant is derived from an adsorption isotherm obtained from the measured values.

When the coating is performed, it is preferred to use a solvent that does not deform the separation membrane, and therefore, water or an aqueous alcohol solution is preferably used. However, many ester group-containing polymers are less soluble in water or an alcohol. Also from this point of view, a copolymer comprising an ester group unit and a water-soluble unit is preferably used as compared with a polymer comprising only vinyl acetate or the like as described above.

In this case, the ratio of the ester unit in the copolymer is preferably from 0.3 to 0.7, more preferably from 0.35 to 0.55 in view of the solubility and the effect of inhibiting the deposition of proteins or blood platelets as described above. Particularly when the water-soluble unit is derived from vinylpyrrolidone, the copolymer is preferably used, because the performance of the separation membrane is hardly reduced by the coating. A copolymer of vinyl acetate and vinylpyrrolidone is particularly preferred. It should be noted that in some cases, a copolymer of vinyl alcohol and vinyl acetate may reduce the membrane performance, because water molecules may be constrained by the effect of hydrogen bonding of the hydroxyl group or the like, so that the membrane may be less permeable to dissolved substances. In addition, when the polysulfone-based separation membrane is coated with the copolymer of vinyl alcohol and vinyl acetate, the performance may be significantly reduced in some cases as compared with the copolymer of vinyl acetate and vinylpyrrolidone, possibly because of the higher adsorption equilibrium constant.

The method of performing insolubilization by irradiation or heat treatment after the coating is preferred, because it can reduce the elution of the ester group-containing polymer. For example, the separation membrane may be irradiated with radiation or treated by heat, while it is immersed in an ester group-containing polymer solution. Alternatively, immersing the separation membrane in a solution of a copolymer comprising a vinylpyrrolidone unit and a hydrophobic unit may be followed by removing the solution and then performing irradiation or heat treatment. When irradiation is performed, a certain amount of a solvent should be present so that the ester group-containing polymer can be easily fixed or insolubilized on the separation membrane. This may be because the solvent can be turned into radicals by irradiation to initiate the conversion of the polymer and the base material of the separation membrane into radicals, so that the copolymer can be crosslinked or insolubilized to the membrane. Therefore, the solvent preferably remains in a weight amount of 0.2 times or more, more preferably 1.0 time or more as much as the dry weight of the separation membrane. In view of handleability, water is preferably used as the solvent. On the other hand, water should not be charged into the separation membrane module so that the risk of the elution can be reduced until the time of the irradiation. Therefore, only the separation membrane should preferably be in wet condition. Specifically, it preferably remains in a weight amount of 6.0 times or less, more preferably 4.0 times or less as much as the dry weight of the separation membrane. After the separation membrane is immersed in an ester group-containing polymer solution, water or the like may be substituted for the solvent, and then irradiation or heat treatment may be performed. The substituted water may also be removed before the irradiation or heat treatment.

When the functional layer of the separation membrane shows an ester carbon peak percentage of 0.1 (at. %) or more and when an insoluble component, which remains after the polymer of the separation membrane is dissolved in a good solvent, shows a water content of 95% or more, preferably 97% or more, the elution of the polymer from the separation membrane can be prevented, and the deposition of proteins can be more effectively inhibited. A certain level of hydrophilicity is necessary for the inhibition of the deposition of proteins. However, when the separation membrane containing a water-soluble polymer such as polyvinylpyrrolidone is free of such an insoluble component, the effect of inhibiting the deposition of some proteins may be not high enough. This may be because proteins may be trapped under a diffuse layer of polyvinylpyrrolidone present at the membrane surface. It is expected that if the diffuse layer is crosslinked to a certain extent, proteins can be prevented from being placed thereunder.

The water content of the insoluble component may be determined as described below. The separation membrane is dried and then dissolved at a concentration of 2% by weight in a good solvent. The solution is filtered with filter paper so that an insoluble component is obtained. After the soluble component is sufficiently washed off with the good solvent, the solvent in the insoluble component is replaced with water. An excess of water is removed, and the weight (w) of the insoluble component containing water is measured. Thereafter, the insoluble component is sufficiently dried and then measured for weight (d). The water content may be calculated from the following formula: water content (%)= $(w-d) \times 100 / w$.

For example, when the separation membrane comprises a polysulfone-based polymer, polyvinylpyrrolidone, and a vinylpyrrolidone/vinyl acetate (6/4) copolymer, dimethylacetamide is used as a good solvent.

To form the insoluble component, an intermolecular or intramolecular crosslinking reaction is preferably performed by applying radiation to the separation membrane or heat-treating the separation membrane. The water content can be adjusted to 95% or more by controlling the dose of exposure to radiation, the heating temperature, or the time. In general, the radiation dose is preferably from 5 to 50 kGy, and the heating condition is preferably from 120 to 300° C., although they depend on the polymer. When radiation is applied, an anti-oxidizing agent may also be used to control the crosslinking reaction. Such an anti-oxidizing agent is described in detail below.

The state of the dispersion of the polymer in the hollow fiber membrane also has an effect on the crosslinking reaction. Therefore, it is preferred that a crosslinking polymer should be finely dispersed in the hollow fiber membrane. Examples of factors having an effect on the state of the dispersion of the polymer in the hollow fiber membrane include the component ratios of the membrane forming stock solution, the agitation rate, the agitation time, and the time from after the dissolution until the membrane production. When the ester group-containing polymer is added to the injection liquid, such factors include the composition of the injection liquid, the temperature of the injection liquid and so on. When coating with the ester group-containing polymer is performed, such factors include the method of coating and so on.

For example, when a hollow fiber membrane comprising polysulfone and polyvinylpyrrolidone is coated with a vinylpyrrolidone/vinyl acetate (6/4) copolymer, the ratio of the polyvinylpyrrolidone in the membrane forming stock solution to the total weight of all the polymers is preferably from 15 to 35% by weight. If the amount of polyvinylpyrrolidone is small, the hydrophilicity level may be low so that the water content may also be low after the crosslinking reaction. If the amount of polyvinylpyrrolidone is too large, it may be impossible to finely disperse polyvinylpyrrolidone, so that the crosslinking reaction may proceed to reduce the water content. The agitation rate may be 30 rpm or more, preferably 50 rpm or more, so that the state of the dispersion of polyvinylpyrrolidone can preferably be improved. The solution should preferably be subjected to spinning within one week after the dissolution, because after the dissolution, micro-phase separation starts and proceeds in the membrane forming stock solution, as time passes, so that it may be impossible to finely disperse polyvinylpyrrolidone. When coating with the ester group-containing polymer is performed, it is effective to generate a pressure difference between the inside and outside of the separation membrane.

It should be noted that even when the adsorption equilibrium constant is high, a low concentration of the ester group-containing polymer solution may make it impossible to sufficiently coat the separation membrane and that if the concentration is too high, the eluted substance may often increase, or the separation membrane performance may often decrease. Specifically, the concentration is generally preferably from 0.0001% by weight to 1% by weight, more preferably from 0.001% by weight to 0.1% by weight, depending on the type of the polymer.

For example, the concentration of a vinylpyrrolidone/vinyl acetate (7/3) copolymer is preferably from 0.05% by weight to 1% by weight. The concentration of a vinylpyrrolidone/vinyl acetate (6/4) copolymer or a vinylpyrrolidone/vinyl acetate (5/5) copolymer is preferably from 0.001% by weight to 1% by weight, more preferably from 0.005% by weight to 0.1% by weight. The concentration of a vinylpyrrolidone/vinyl acetate (3/7) copolymer or polyvinyl acetate is preferably from 0.001% by weight to 0.5% by weight. Although described in detail below, an anti-oxidizing agent may be allowed to coexist so that the effect of inhibiting the deposition of proteins or blood platelets can be produced even when the lower limit of the concentration is further decreased.

After the immersion, the ester group-containing polymer solution or water may be removed using any of various methods such as drying under reduced pressure, drying at high temperature, air blow drying at low temperature, and blow drying. It is known that when radiation is applied in the presence of oxygen, oxygen radicals are generated to decompose a polymer material used as the base material of a separation membrane. Therefore, when radiation is applied, the oxygen concentration around the separation membrane is preferably 10% or less. In the process of applying radiation to a separation membrane module, for example, the oxygen concentration may be reduced by purging air from the module using nitrogen gas and sealing the module, and then radiation may be applied.

Concerning the timing of the coating, the separation membrane may be coated with the ester group-containing polymer, before the membrane is incorporated into the module, or the ester group-containing polymer solution may be charged into the separation membrane module so that coating can be achieved. After the coating, irradiation with radiation or heat treatment may be performed as described above.

In an embodiment of the invention, the radiation to be used may be α radiation, β radiation, γ radiation, X-ray, ultraviolet radiation, electron beam, or the like. A blood purification module such as an artificial kidney must be sterilized, and in recent years, radiation sterilization using γ radiation or electron beams has been frequently used, because of its low residual toxicity and convenience. Therefore, when the separation membrane is coated with the ester group-containing polymer, sterilization and the insolubilization of the copolymer can be simultaneously achieved by the sterilization process.

When the sterilization and modification of the base material are simultaneously performed, a radiation dose of 15 kGy or more is preferably used. This is because 15 kGy or more is effective in sterilizing a blood purification module with γ radiation. However, if the radiation dose is 100 kGy or more, the three-dimensionally crosslinked structure or the ester moiety of the ester group-containing polymer may be decomposed, so that its compatibility with blood may be reduced.

In the steps of coating the separation membrane with the ester group-containing polymer and insolubilizing the polymer with radiation, the solution may also contain a component other than the polymer, such as an anti-oxidizing agent. Alternatively, after the separation membrane is coated with the ester group-containing polymer, an anti-oxidizing agent may be brought into contact with the polymer.

The addition of the anti-oxidizing agent makes it possible to control the amount of generation of radicals. For example, in the process of producing a blood purification module, when the insolubilization and the sterilization are simultaneously performed by irradiation, an anti-oxidizing agent may be used in combination with the irradiation, so that the radiation dose for either of them can be prevented from degrading the separation membrane.
In the process of coating the separation membrane with the ester group-containing polymer, the addition of an anti-oxidizing agent also makes it possible to reduce the amount of the ester group-containing polymer to be added. For example, when a vinylpyrrolidone/vinyl acetate (6/4) copolymer or a vinylpyrrolidone/vinyl acetate (5/5) copolymer is used in combination with an anti-oxidizing agent such as ethanol, the lower limit of the preferred range stated above can be reduced to 1/10 or less. This may be because the anti-oxidizing agent can inhibits a radiation-induced decomposition reaction of the ester group. As used herein, the term "anti-oxidizing agent" refers to a molecule having the property of easily donating electrons to other molecules. Examples of the anti-oxidizing agent include, but are not limited to, water-soluble vitamins such as vitamin C; polyphenols; alcohols such as methanol, ethanol, propanol, ethylene glycol, propylene glycol, and glycerin; saccharides such as glucose, galactose, mannose, and trehalose; inorganic salts such as sodium hydrosulfite, sodium pyrosulfite, and sodium dithionate; and uric acid, cysteine, and glutathione. These anti-oxidizing agents may be used alone or in combination of two or more. When the method of the invention is used for medical devices, an anti-oxidizing agent with low toxicity is preferably used in view of the safety.

The concentration of the anti-oxidizing agent-containing solution depends on the type of the anti-oxidizing agent used, the radiation dose, and so on. If the concentration of the anti-oxidizing agent is too low, radicals generated from the solvent cannot be sufficiently eliminated, so that it may be impossible to prevent the degradation of the separation membrane and so on. If a large amount of an anti-oxidizing agent is added, radicals may be completely eliminated, so that the amount of the copolymer fixed on the separation membrane may be reduced, which may increase the eluted substance or make it impossible to sufficiently obtain the effect of inhibiting the deposition of proteins or blood platelets. Thus, ethanol, n-propanol, 2-propanol, ethylene glycol, propylene glycol, or glycerin is preferably used as the anti-oxidizing agent, and it is preferably used at a concentration in the range of 0.01% by weight to 90% by weight. In particular, ethanol, n-propanol, or 2-propanol is preferably used at a concentration of 0.01% by weight to 10% by weight, more preferably 0.05% by weight to 1% by weight. Propylene glycol or glycerin is preferably at a concentration of 0.1% by weight to 90% by weight, more preferably 0.5% by weight to 70% by weight.

The separation membrane is capable of selectively removing specific substances from a liquid being treated, such as blood or an aqueous solution, by adsorption, size exclusion or the like.

The separation membrane has high resistance to deposition and therefore is suitable for use as a water treatment separation membrane or a biological component separation membrane. In particular, the separation membrane is suitable for a blood purification module such as an artificial kidney. As used herein, the term "blood purification module" refers to a module having the function of removing waste products or harmful substances from blood being extracorporeally circulated, examples of which include an artificial kidney and an exotoxin adsorption column. The module for artificial kidney may be of a coil type, a flat plate type, or a hollow fiber membrane type, preferably a hollow fiber membrane type in view of treatment efficiency or the like.

The separation membrane module may be produced by various methods depending on the intended use. The production process may be typically divided into a process of producing the separation membrane and a process of incorporating the separation membrane into a module.

An example of the method of producing an artificial kidney, as a blood purification module, is described below. A method of producing a hollow fiber membrane as the separation membrane includes dissolving polysulfone and polyvinylpyrrolidone (preferably 20:1 to 1:5 in weight ratio, more preferably 5:1 to 1:1 in weight ratio) in a mixed solvent of a good solvent for polysulfone (preferably N,N-dimethylacetamide, dimethyl sulfoxide, dimethylformamide, N-methylpyrrolidone, or dioxane) and a poor solvent to form a stock solution (preferably with a concentration of 10 to 30% by weight, more preferably 15 to 25% by weight); discharging the stock solution from a double annular nozzle, while allowing an injection liquid to flow through the inside of the double annular nozzle; allowing the resulting membrane to pass through a dry unit; and then introducing the membrane into a coagulation bath. In this process, the humidity of the dry unit has a certain effect. Therefore, water may be supplemented from the outer surface of the membrane during the passing through the dry unit, so that the phase-separation behavior can be promoted near the outer surface to increase the pore size, which may result in a reduction in resistance to permeation/diffusion during dialysis. However, if the relative humidity is too high, the stock solution may be predominantly coagulated at the outer surface, so that the pore size may be rather reduced, which may tend to result in an increase in resistance to permeation/diffusion during dialysis. Thus, the relative humidity is preferably from 60 to 100% RH. The injection liquid composition to be used is preferably based on the solvent used in the stock solution, in view of process suitability. Concerning the concentration of the injection liquid, for example, dimethylacetamide is preferably used at a concentration of 45 to 80% by weight, more preferably 60 to 75% by weight in an aqueous solution.

A non-limiting example of the method for building the hollow fiber membrane into the module is shown below. First, the hollow fiber membrane is cut into the desired length, and a desired number of the cut pieces are bundled and then placed in a tubular case. Thereafter, both ends are temporarily capped, and a potting agent is added to both ends of the hollow fiber membrane. In this process, a method of adding a potting agent while rotating the module by means of a centrifugal machine is preferred, because the potting agent can be uniformly charged. After the potting agent is solidified, both ends are cut in such a manner that openings can be formed at both ends of the hollow fiber membrane, so that a hollow fiber membrane module is obtained.

The invention, according to exemplary embodiments, is described by illustration in the examples below, which are not intended to limit the scope of the invention.

EXAMPLES

The invention is described by the examples and the comparative examples below, which are not intended to limit the scope of the invention.

1. Measurement Methods (1) X-Ray Electron Spectroscopy (ESCA)

The hollow fiber membrane was sliced into a semi-cylindrical shape with a single-edged knife, and the measurement was performed at three points of each of the inner surface and the outer surface of the hollow fiber membrane. The measurement sample was rinsed with ultrapure water, then dried at room temperature at 0.5 Torr for 10 hours and then subjected to the measurement. The following analyzer and conditions were used.
Analyzer: ESCA LAB220iXL
Excitation X-ray: monochromatic Al K$\alpha$1,2 radiation (1486.6 eV)
X-ray diameter: 0.15 mm
Photoelectron escape angle: 90° (the tilt of the detector relative to the sample surface).

The ester carbon content was determined as described below. The ester (COO) carbon peak was observed at an energy +4.0 to +4.2 eV higher than the main C1s peak derived from CH or C—C (at about 285 eV). Therefore, after peak deconvolution was performed, the ratio of the corresponding peak area to the peak area of all elements (all elements except for the hydrogen atom, which was not detectable) was calculated so that the ester carbon content (at. %) was determined.

When the base material of the separation membrane was polysulfone, the vinylpyrrolidone unit content of the surface was calculated from a vinylpyrrolidone unit molecular weight of 111, a polysulfone unit molecular weight of 442, the nitrogen content (a (at. %)), and the sulfur content (b (at. %)) according to the following formula: surface vinylpyrrolidone content (% by weight)=(a×111/(a×111+b×442))×100

When the base material of the separation membrane is polyacrylonitrile, the number of carbons in the acryl unit is 3, the number of nitrogen atoms in the acryl unit is 1, the number of carbon atoms in vinylpyrrolidone is 6, the number of oxygen atoms 1 in vinylpyrrolidone is 1, and the number of nitrogen atoms in vinylpyrrolidone is 1. The vinylpyrrolidone unit content of the surface can be calculated from the ratio between them.

(2) Measurement of the Vinyl Acetate Unit Content Ratios of the Surface and the Inside of the Separation Membrane The content of the ester group-containing polymer in the separation membrane surface may be determined using ESCA as described in the section (1). The vinyl acetate unit content ratio of the surface was measured using ESCA. The analyzer and the conditions were the same as those in the section (1).

The ester (COO) peak is observed in the C1s peaks for the ester carbon content (at. %), which are obtained in the same manner as in the section (1), and therefore, the vinyl acetate unit content ratio is obtained after the peak deconvolution. One sulfur atom is present per repeating unit in polysulfone, and therefore, the polysulfone content is obtained by determining the sulfur content. Thus, the following formula was used: surface vinyl acetate unit content ratio=(ester group content (at. %))/(sulfur content (at. %))

The vinyl acetate unit content ratio of the inside was determined by performing ATR measurement. The measurement conditions were a resolution of 4 and a cumulative number of 64. The intensity ($A_{CO}$) of the C=O peak derived from the ester group at about 1730 cm$^{-1}$ and the intensity ($A_{CC}$) of the C=C absorption peak derived from the benzene ring of polysulfone at about 1580 cm$^{-1}$ were determined. The ATR measurement depth is from the surface to about 2 to 3 μm.

Polysulfone and polyvinyl acetate were dissolved at various concentrations in N,N-dimethylacetamide. Drops of each of the solutions with various concentrations were put on a glass plate heated at 110° C. by means of a hot plate and cast into a thickness of 203 μm. After the casting, the resulting film was allowed to stand on the hot plate for 5 minutes. After the solvent was evaporated, the glass plate with the film was immersed in a water bath, so that a transparent film was obtained (the immersion in the water bath is for easy peeling off of the film from the glass plate).

The film was subjected to the ATR measurement, and a calibration curve was obtained between the intensity ratio ($A_{CO}$)/($A_{CC}$) and the vinyl acetate unit content ratio.

The inner surface of the hollow fiber membrane was subjected to the ATR measurement, and the vinyl acetate unit content ratio of the inside was determined from the intensity ratio ($A_{CO}$)/($A_{CC}$) using the calibration curve.

In the case of polyacrylonitrile, the ratio between $A_{CO}$ and the intensity ($A_{CN}$) of the C≡N peak derived from the nitrile group at about 2,200 cm$^{-1}$ was used. A calibration curve was obtained with films in the same manner as described above, and the vinyl acetate unit content ratio of the inside was determined from the intensity ratio using the calibration curve.

(3) Method for Measuring Ester Group Distribution by Infrared Absorption Spectrometry The hollow fiber membrane was sliced into a semi-cylindrical shape with a single-edged knife, rinsed with ultrapure water, and then dried at room temperature at 0.5 Torr for 10 hours. The inner surface of the dried hollow fiber membrane was measured by microscope ATR method using IRT-3000 manufactured by JASCO Corporation. The measurement was performed in a field region (aperture) of 100 μm×100 μm with a cumulative number of 30 per one point. The aperture was shifted by 3 μm, and five points (lengthwise) by five points (widthwise) (25 points in total) were measured. A base line was drawn on the resulting spectrum in the wavelength range of 1,549 to 1,620 cm$^{-1}$, and the peak area surrounded by the base line and the positive part of the spectrum was determined to be the infrared absorption peak area $A_{CC}$ derived from the benzene ring C=C of polysulfone. Similarly, a base line was drawn on the spectrum in the range of 1,711 to 1,759 cm$^{-1}$, and the infrared absorption peak area $A_{CO}$ derived from the ester group C=O was determined.

The above process was performed on three different hollow fibers per one module, and the measurement was performed at three different places per one hollow fiber. The average $(A_{CO})/(A_{CC})$ and the rate of the measurement points at which the ratio is 0.001 or less were calculated.

(4) Calculation of Adsorption Equilibrium Constant

The adsorption equilibrium constant was determined by surface plasmon resonance measurement. After an Au sensor chip manufactured by GE Healthcare Bio-Sciences was fixed on a spin coater, one or two drops of a chlorobenzene solution of 0.1% by weight polysulfone (Udel-P3500, Amoco) or a dimethyl sulfoxide solution of 0.1% by weight polyacrylonitrile were put on the chip with a Pasteur pipette. Immediately after that, the spin coater was rotated at 3,000 rpm for 1 minute, so that an Au sensor chip having a thin layer of polysulfone or polyacrylonitrile on the surface was prepared. The sensor chip was placed in BIACORE 3000 manufactured by GE Healthcare Bio-Sciences. After the sensor chip was washed with water for 2,000 seconds, the processes described below were repeatedly performed with different aqueous polymer solutions at each of concentrations of 5, 10, 50, 100, 500, and 1,000 ppm.

1. Each of different aqueous polymer solutions was allowed to flow at a rate of 20 μL/minute in a total amount of 750 μL, so that the polymer was adsorbed to the surface of polysulfone or polyacrylonitrile.
2. Washing with water was performed for 2,000 seconds.
3. Triton with a concentration of 0.025% by weight was allowed to flow at a rate of 20 μL/minute in a total amount of 750 μL so that each adsorbed polymer was peeled off.
4. Washing with water was performed for 2,000 seconds.

The amount of the polymer adsorbed to the surface of polysulfone or polyacrylonitrile was determined as described below. The value obtained after water washing for 2,000 seconds immediately after the insertion of the sensor chip was normalized as 0, and the amount of the polymer adsorbed to the surface was defined as the value of each difference obtained at the end of the process 2. When the value obtained at end of the process 4 was higher than the value obtained after water washing immediately after the insertion of the sensor chip, it was assumed that each polymer was not completely peeled off with 0.025% by weight Triton, and the increase was added to the adsorbed amount. The above processes were repeated at concentrations of 5 to 1,000 ppm, and the adsorption equilibrium constant was calculated from the resulting adsorption isotherm (in which the abscissa axis represents the concentration of each of different polymers, and the ordinate axis represent the adsorbed amount) by least squares method for fitting, using a general solution adsorption model for a polymer and the adsorption surface thereof (approximation by Freundlich equation (formula 1)).

$$Q=KC^n \quad \text{(formula 1)}$$

(Q: adsorbed amount per unit area, K: adsorption equilibrium constant, n: Freundlich constant).

(5) Measurement of the Water Content of Insoluble Component

The hollow fiber membrane was dried and then dissolved at a concentration of 2 g/vol % in dimethylacetamide with stirring for 5 hours or more. The insoluble component was filtered off with filter paper (ADVANTEC® No. 7 manufactured by Toyo Roshi Kaisha, Ltd.), and then the soluble component was sufficiently washed off with dimethylacetamide. The insoluble component (gelatinous material) was collected into a centrifugation tube and further stirred enough with dimethylacetamide. Thereafter, the gel was precipitated by centrifugation, and the supernatant was removed. This process was repeated three times or more. Thereafter, the supernatant was removed, and then pure water was added to the gel. After sufficient stirring, the gel was precipitated by centrifugation, and the supernatant was removed. This process was repeated five times, and then dimethylacetamide was replaced with pure water. An excess of water was removed, and the weight (w) of the water-containing gel was measured. The resulting water-containing gel was lyophilized for 24 hours or more and measured for weight (d) after it was completely dried. The water content was calculated from the following formula: water content (%)=(w−d)×100/w.

(6) Method for Testing Deposition of Human Platelets on Hollow Fiber Membrane

A double-side tape was bonded to an 18 mmφ polystyrene circular plate, and the hollow fiber membrane was fixed thereon. The attached hollow fiber membrane was sliced into a semi-cylindrical shape with a single-edged knife so that the inner surface of the hollow fiber membrane was exposed. It should be carefully performed, because if there is dirt, a scratch, a fold, or the like on the inner surface of the hollow fiber, platelets may be deposited on such a portion so that the evaluation may not be correctly performed. The circular plate was attached to a cylindrical cut piece of Falcon® tube (No. 2051, 18 mmφ) so that the hollow fiber membrane-carrying surface was placed inside the cylinder, and the gap was filled with Parafilm. The interior of the cylindrical tube was washed with a saline solution and then filled with a saline solution. Heparin was added at a concentration of 50 U/ml to human venous blood immediately after the blood sampling. After the saline solution was discharged from the cylindrical tube, 1.0 ml of the blood was placed in the cylindrical tube within 10 minutes after the sampling and shaken at 37° C. for 1 hour. Thereafter, the hollow fiber membrane was washed with 10 ml of a saline solution, and the blood component was fixed thereon with a 2.5% by weight glutaraldehyde saline solution and washed with 20 ml of distilled water. The washed hollow fiber membrane was dried at room temperature under a reduced pressure of 0.5 Torr for 10 hours. The hollow fiber membrane was then bonded to the sample stage of a scanning electron microscope with a double-side tape. A Pt—Pd thin film was then formed on the surface of the hollow fiber membrane by sputtering, so that a sample was obtained. The inner surface of the hollow fiber membrane sample was observed with a field emission-type scanning electron microscope (S800 manufactured by Hitachi, Ltd.) at a magnification of 1,500 times, and the number of the deposited platelets per field (4.3×10$^3$ μm$^2$) was counted. The number of the deposited platelets (/4.3×10³ μm²) was defined as the average of the numbers of the deposited platelets which were counted in ten different fields at and around the longitudinal center of the hollow fiber. The longitudinal ends of the hollow fiber were omitted from the objects to be measured for the number of deposits, because blood tended to stay thereon.

If the number of the deposited platelets is 40 (/4.3×10³ μm²) or less, preferably 20 (/4.3×10³ μm²) or less, more preferably 10 (/4.3×10³ μm²) or less, the material has good anti-thrombogenetic properties.

(7) Measurement of Relative Rate of Deposition of Fibrinogen

Concerning the deposition of proteins on the hollow fiber membrane, the relative rate of adsorption of fibrinogen, a coagulating system protein, was measured.

Thirty six hollow fiber membranes were inserted into a plastic tube, and both ends were fixed with an adhesive, so that a plastic tube mini-module with an effective length of 100 mm was prepared, which was sufficiently washed with pure water.

Citric acid was then added at a concentration of 10% by volume to human venous blood immediately after the blood sampling. The blood was centrifuged at 4° C. at 3,000 rpm for 15 minutes, so that plasma was obtained.

One mL of the plasma was circulated through the module at a flow rate of 0.5 mL/minute for 2 hours. A 24 cm long piece of the hollow fiber was cut from the mini-module, and the cut piece was cut into about 1 mm long small pieces, which were placed in an Eppen tube and washed with a phosphate buffer solution (hereinafter abbreviated as PBS) (1 mL×3 times, when the blood was left, the washing was repeated). Tween 20 (KATAYAMA CHEMICAL, LTD.) was adjusted to 0.05% by weight with PBS (hereinafter, the preparation is abbreviated as PBS-T). Skimmed milk was dissolved at a concentration of 0.1% by weight in PBS-T, and washing with the solution was performed three times. An anti-human fibrinogen (HPR) antibody was diluted 10,000 times with the 0.1% by weight skimmed milk/PBS-T solution. After 1 mL of the dilution was added to the tube, rotation and agitation were performed at room temperature for 2 hours with a rotator. After washing with the 0.1% by weight skimmed milk/PBS-T solution twice, washing with the 0.1% by weight skimmed milk/PBS solution was performed twice. One mL of TBM one solution was added and agitated with a micro-mixer. While the degree of color development was observed, 200 μL of 6 N hydrochloric acid was added to stop the reaction (the reaction was controlled so that the absorbance of the control mentioned below could fall within the range of 1 to 1.5). The absorbance was measured at 450 nm. The control used was an artificial kidney TORAYSULFONE TS-1.6UL manufactured by TORAY INDUSTRIES, INC. The relative rate of deposition of fibrinogen was calculated from the absorbance (Ac) of the control and the absorbance of the sample (As) according to the following formula: relative rate of deposition of fibrinogen (%)=(As/Ac)×100

(8) Measurement of $\beta_2$-Microglobulin ($\beta_2$-MG) Clearance

Clearance of $\beta_2$-microglobulin was measured for the evaluation of the performance of the hollow fiber membrane. The $\beta_2$-microglobulin is a protein to be removed during dialysis treatment. In recent year, the clearance of it has been frequently used as an index of membrane performance. In the examples, therefore, the clearance value is used as an index.

Disodium ethylenediamine tetraacetate was added to bovine blood, and the hematocrit and total protein content of the bovine blood were adjusted to 30±3% and 6.5±0.5 g/dL, respectively.

Then, $\beta_2$-microglobulin was added at a concentration of 1 mg/l to the bovine blood and stirred. The resulting bovine blood was divided into a 2 L aliquot for circulation and a 1.5 L aliquot for clearance measurement.

Figure 2:
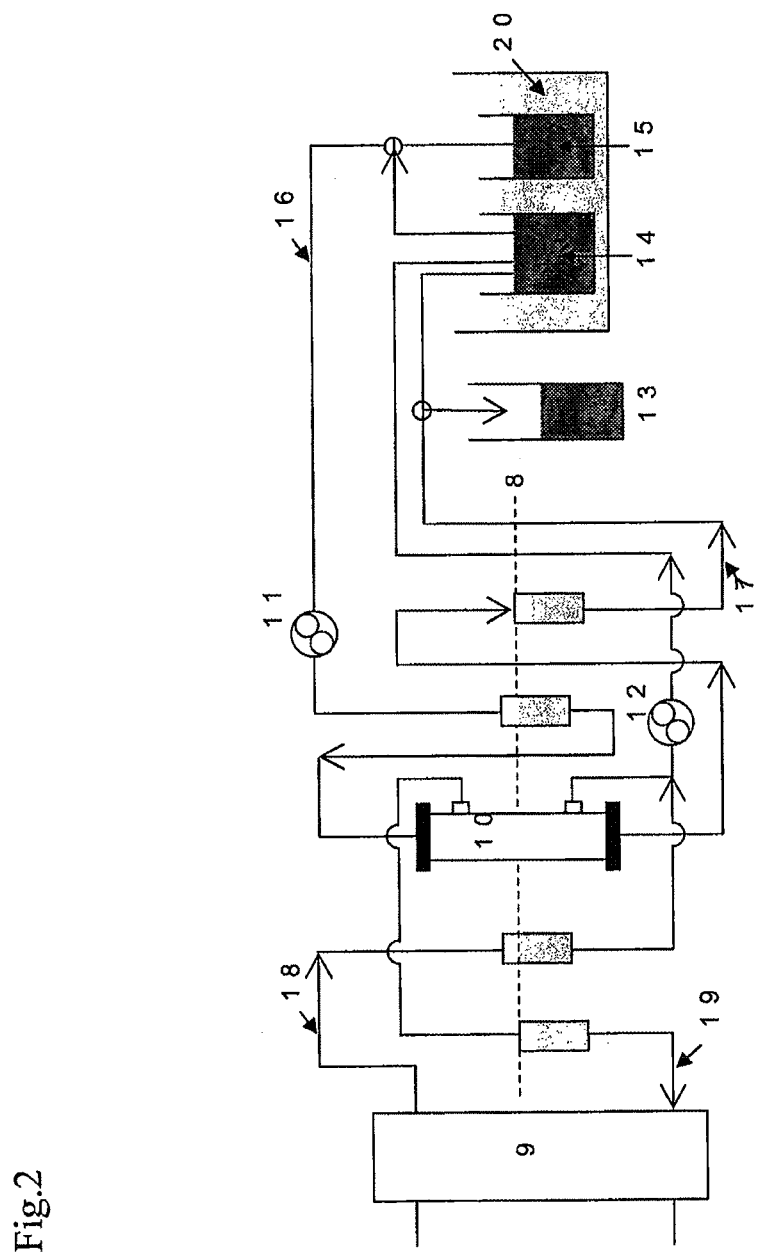
FIG. 2 illustrates a circuit used in $\beta_2$-microglobulin clearance measurement performed in Examples 1 to 10 and Comparative Examples 1 to 7.

A circuit was configured as shown in FIG. 2. TR2000S manufactured by TORAY MEDICAL CO., LTD. was used for a dialyzer. In FIG. 2, TR2000S corresponds to the Bi pump, the F pump, and the dialyzer.

Dialyzate solutions A and B (Kindaly solution AF No. 2 manufactured by Fuso Pharmaceutical Industries, Ltd.) were placed in the dialyzer. RO water was allowed to flow from the dialyzate side to the blood side. The dialyzate concentration, the temperature, and the dialyzate side flow rate were set at 13-15 mS/cm, 34° C. or more, and 500 ml/minute, respectively.

The water removal rate of the dialyzer was set at 10 ml/(min·m²). The inlet of the Bi circuit was placed in a circulation beaker containing 2 L of the bovine blood (37° C.) prepared as described above, and the Bi pump was started. After the liquid from the outlet of the Bo circuit was discarded for 90 seconds, the outlet of the Bo circuit and the outlet of the Do circuit were immediately placed in circulation beakers to form a circulation state.

Subsequently, the F pump of the dialyzer was started. After the circulation was performed for 1 hour, the Bi and F pumps were stopped.

The inlet of the Bi circuit was then placed in the bovine blood prepared as described above for clearance measurement, and the outlet of the Bo circuit was placed in a beaker for discharge. The liquid from the outlet of the Do circuit was discarded.

The Di pump was started. The blood pump was also started, and the space between the trap and the Bi chamber was opened.

Two minutes after the start, 10 ml of a sample was collected from the bovine blood (37° C.) for clearance measurement and named Bi liquid. Four minutes and 30 seconds after the start, 10 ml of a sample was collected from the outlet of the Bo circuit and named Bo liquid. These samples were stored in a freezer at −20° C. or less.

For each liquid, the clearance was calculated from the concentration of $\beta_2$-microglobulin according to the formula below. Since the measurement may vary with the lot of bovine blood, bovine blood from the same lot was used for the data in the examples.

Co (ml/minute)=(CBi−CBo)×$Q_B$/CBi, wherein Co is $\beta_2$-microglobulin clearance (ml/minute), CBi is the concentration of $\beta_2$-microglobulin in Bi liquid, CBo is the concentration of $\beta_2$-microglobulin in Bo liquid, and $Q_B$ is the flow rate of the Bi pump (ml/minute).

2. Preparation of Hollow Fiber Membrane Module (1) Hollow Fiber Membrane of Polysulfone/Polyvinylpyrrolidone (PSf/PVP) Mixture Sixteen parts by weight of polysulfone (Udel-P3500, Amoco), 3 parts by weight of polyvinylpyrrolidone (K30, International Special Products (hereinafter abbreviated as ISP)), and 3 parts by weight of polyvinylpyrrolidone (K90, ISP) were dissolved with heating in 77 parts by weight of dimethylacetamide and 1 part by weight of water, so that a membrane forming stock solution was obtained.

The stock solution was fed to a spinning nozzle at a temperature of 50° C., and an injection liquid, which was a solution of 63 parts by weight of dimethylacetamide and 37 parts by weight of water, was discharged from a double annular slit tube with an outer diameter of 0.35 mm and an inner diameter of 0.25 mm, so that a hollow fiber membrane was formed. The hollow fiber membrane was then allowed to pass through a 350 mm dry-zone atmosphere at a temperature of 30° C. and a dew point of 28° C. and through a coagulation bath of 20% by weight dimethylacetamide and 80% by weight water at a temperature of 40° C. The hollow fiber membrane was then allowed to pass through a water washing process at 60 to 75° C. for 90 seconds, a drying process at 130° C. for 2 minutes, and a crimping process at 160° C. The resulting hollow fiber membrane (hollow fiber membrane 1) was wound into a bundle.

As a result of elemental analysis and calculation, the polyvinylpyrrolidone content of the inner surface (namely, the functional layer) of the hollow fiber membrane was 23% by weight, and the content of polyvinylpyrrolidone in the membrane was 3.1% by weight. The hollow fiber membrane was charged into a case so as to have a total membrane area of 1.6 m$^2$, and both ends of the hollow fiber membrane were fixed onto the ends of the case with a potting material. The ends of the potting material were partially cut in such a manner that openings were formed at both ends of the hollow fiber membrane, so that a hollow fiber membrane module was obtained.

(2) Polysulfone (PSf) Hollow Fiber Membrane

Eighteen parts by weight of polysulfone (Udel-P3500, Amoco) was dissolved with heating in 81 parts by weight of dimethylacetamide and 1 part by weight of water, so that a membrane forming stock solution was obtained.

The stock solution was fed to a spinning nozzle at a temperature of 50° C., and an injection liquid, which was a solution of 63 parts of dimethylacetamide and 37 parts of water, was discharged from a double annular slit tube with an outer diameter of 0.35 mm and an inner diameter of 0.25 mm, so that a hollow fiber membrane was formed. The hollow fiber membrane was then allowed to pass through a 350 mm-long dry-zone atmosphere at a temperature of 30° C. and a dew point of 28° C. and through a coagulation bath of 20% by weight dimethylacetamide and 80% by weight water at a temperature of 40° C. The hollow fiber membrane was then allowed to pass through a water washing process at 60° C. for 90 seconds. The resulting hollow fiber membrane (hollow fiber membrane 2) was wound into a bundle.

(3) Chloroacetamidemethylated Sulfone-Containing Hollow Fiber Membrane

A nitrobenzene solution of polysulfone (Udel-P3500, Amoco) was prepared at a concentration of 7.13 wt %. To 175.3 g of the nitrobenzene solution cooled at 8° C. was added 33 g of a sulfuric acid solution of 5.30 wt % of N-methylol-2-chloroacetamide, which was separately prepared with stirring at −5° C. for 30 minutes, and the mixture was allowed to react at 8° C., so that chloroacetamidemethylated polysulfone (with a chloroamidemethyl substitution degree of 0.39) was obtained.

Eighteen parts by weight of polysulfone (Udel-P3500, Amoco), 2 parts by weight of chloroacetamidemethylated polysulfone, and 10 parts by weight of PVP K30 (ISP) were dissolved with heating in 69 parts by weight of dimethylacetamide and 1 part by weight of water, so that a membrane forming stock solution was obtained.

The stock solution was fed to a spinning nozzle at a temperature of 40° C., and an injection liquid, which was a solution of 35 parts of dimethylacetamide and 65 parts of water, was discharged from a double annular slit tube with an outer diameter of 0.35 mm and an inner diameter of 0.25 mm, so that a hollow fiber membrane was formed. The hollow fiber membrane was then allowed to pass through a 300 mm-long dry-zone atmosphere at a temperature of 27° C. and a dew point of 11° C. and through a coagulation bath of 100% by weight water at a temperature of 40° C. The resulting hollow fiber membrane (hollow fiber membrane 3) was wound into a bundle.

(4) Experiment of Addition of Polymer to Injection Liquid

Eighteen parts by weight of polysulfone (Udel-P3500, Amoco, 47,000 in weight average molecular weight) and 9 parts by weight of polyvinylpyrrolidone (K30, International Special Products (hereinafter abbreviated as ISP)) were dissolved with heating in 72 parts by weight of dimethylacetamide and 1 part by weight of water, so that a membrane forming stock solution was obtained.

An injection liquid was prepared by dissolving 10 parts by weight of a vinylpyrrolidone/vinyl acetate (6/4) copolymer (Kollidon VA64 manufactured by BASF) in a solution of 63 parts by weight of dimethylacetamide and 37 parts by weight of water.

The stock solution was fed to a spinning nozzle at a temperature of 50° C., and the injection liquid was discharged from a double annular slit tube with an outer diameter of 0.35 mm and an inner diameter of 0.25 mm, so that a hollow fiber membrane was formed. The hollow fiber membrane was then allowed to pass through a 350 mm dry-zone atmosphere at a temperature of 30° C. and a dew point of 28° C. and through a coagulation bath of 20% by weight dimethylacetamide and 80% by weight water at a temperature of 40° C. The hollow fiber membrane was then allowed to pass through a water washing process at 60 to 75° C. for 90 seconds, a drying process at 130° C. for 2 minutes, and a crimping process at 160° C. The resulting hollow fiber membrane (hollow fiber membrane 4) was wound into a bundle.

A hollow fiber membrane (hollow fiber membrane 5) was also prepared as described above, except that Kollidon VA64 was not added to the solution composition to be used as the injection liquid.

(5) Polyacrylonitrile (PAN) Hollow Fiber Membrane

A mixture of 15 parts by weight of polyacrylonitrile with a weight average molecular weight of 600,000 and 85 parts by weight of dimethyl sulfoxide was prepared and stirred at 103° C. for 16 hours, so that a spinning stock solution was prepared. The resulting stock solution was discharged at a rate of 1.2 g/minute from an annular slit-type hollow nozzle (outer diameter/inner diameter=0.6/0.3 mmϕ) into the air. At the same time, nitrogen gas was injected into the hollow at a pressure of 74 mmAq. The resulting hollow fiber membrane (hollow fiber membrane 6) was then introduced into water at 50° C. and wound into a bundle.

3. Preparation of Allylamine/Vinyl Acetate Copolymer

A solution of 47 g of allylamine hydrochloride in 110 g of methanol was prepared, and 103 g of vinyl acetate was added to the solution. After 41 g of azobisisobutyronitrile as a polymerization initiator was added thereto, the mixture was heated to 60° C. and allowed to react for 24 hours. Thereafter, 41 g of azobisisobutyronitrile was further added, and the mixture was further allowed to react for 24 hours at 60° C. At the end of the polymerization reaction, the remaining monomers and the homopolymer were removed, so that an allylamine hydrochloride-vinyl acetate copolymer was obtained. As a result of elemental analysis, the allylamine content of the copolymer was determined to be 28% by mole.

In Examples 1 to 12 and Comparative Examples 1 to 8 below, the hollow fiber membrane of a polysulfone/polyvinylpyrrolidone (PSf/PVP) mixture (hollow fiber membrane 1) was used.

Example 1

Five hundred mL of an aqueous solution of 0.1% by weight of a vinylpyrrolidone/vinyl acetate (6/4) copolymer (Kollidon VA64 manufactured by BASF) was allowed to pass through the hollow fiber membrane module prepared as described above from the blood side inlet (Bi) to the blood side outlet (Bo). Then, 500 mL of the solution was allowed to pass from the blood side inlet (Bi) to the dialyzate side inlet (Di), so that VA64 was accumulated on the inner surface of the hollow fiber membrane. In this process, the liquid temperature was 30° C., and the flow rate was 500 mL/minute. The VA64 placed in the hollow fiber membrane was further accumulated on the inner surface by pressing the filling liquid from the dialyzate side to the blood side with compressed air at 100 kPa. Thereafter, the filling liquid on the blood side was blown so that the aqueous solution was held only in the hollow fiber membrane. In addition, nitrogen was blown for 1 minute into each of the dialyzate side and the blood side so that the air in the module was replaced with nitrogen. The VA64 was fixed on the membrane by applying 25 kGy of γ radiation to the whole of the module. The hollow fiber was cut from the module and subjected to each test. The measurement of the ester carbon content was performed twice under the same conditions. The results are shown in the table below. A large amount of VA64 was successfully and uniformly localized at the surface of the functional layer, and high resistance to the deposition of platelets and high $\beta_2$-microglobulin clearance performance were obtained. The adsorption equilibrium constant of Kollidon VA64 on a polysulfone film is shown in the table.

Example 2

The same process as in Example 1 was performed, except that an aqueous solution of 0.01% by weight of a vinylpyrrolidone/vinyl acetate (6/4) copolymer (Kollidon VA64 manufactured by BASF) was used instead. The measurement of the ester carbon content was performed twice under the same conditions. The results are shown in the table below. A large amount of VA64 was successfully and uniformly localized at the surface of the functional layer, and high resistance to the deposition of platelets and high $\beta_2$-microglobulin clearance performance were obtained. The $\beta_2$-microglobulin clearance performance was higher in this example than in Comparative Example 1. This may be because the functional layer surface is covered with VA64 in such a degree that the effect of inhibiting the deposition of proteins and so on is higher than the effect of reducing the pore size, so that the performance is less reduced by clogging of the membrane with proteins. The water content of the insoluble component was 95.2%, and the relative rate of adsorption of fibrinogen was 65%.

Example 3

The same process as in Example 1 was performed, except that an aqueous solution of 0.001% by weight of a vinylpyrrolidone/vinyl acetate (6/4) copolymer (Kollidon VA64 manufactured by BASF) was used instead. The measurement of the ester carbon content was performed twice under the same conditions. The results are shown in the table below. A large amount of VA64 was successfully localized at the surface of the functional layer, and high resistance to the deposition of platelets and high $\beta_2$-microglobulin clearance performance were obtained. The resistance to the deposition of platelets was slightly lower in this example than in Example 1 or 2. This may be because the ester group content of the functional layer surface is lower in this example than in Example 1 or 2, so that the ester group distribution is uneven.

Example 4

The same process as in Example 1 was performed, except that an aqueous solution of a mixture of 0.001% by weight of a vinylpyrrolidone/vinyl acetate (6/4) copolymer (Kollidon VA64 manufactured by BASF) and 0.1% by weight of ethanol was used instead. The measurement of the ester carbon content was performed twice under the same conditions. The results are shown in the table below. A large amount of VA64 was successfully and uniformly localized at the surface of the functional layer, and high resistance to the deposition of platelets and high $\beta_2$-microglobulin clearance performance were obtained. The resistance to the deposition of platelets was higher in this example than in Example 3, even though the VA64 concentrations were the same in the treatment. This may be because ethanol is effective in protecting the ester group from γ radiation. The water content of the insoluble component was 97.3%, and the relative rate of adsorption of fibrinogen was 28%. As compared with Example 1, the deposition of fibrinogen was reduced to a half or less, even though the number of the deposited platelets was the same.

Example 5

The same process as in Example 1 was performed, except that an aqueous solution of a mixture of 0.0005% by weight of a vinylpyrrolidone/vinyl acetate (6/4) copolymer (Kollidon VA64 manufactured by BASF) and 0.1% by weight of ethanol was used instead. The results are shown in the table below. A large amount of VA64 was successfully and uniformly localized at the surface of the functional layer, and high resistance to the deposition of platelets and high $\beta_2$-microglobulin clearance performance were obtained.

Example 6

An aqueous solution of 0.01% by weight of a vinylpyrrolidone/vinyl acetate (6/4) copolymer (Kollidon VA64 manufactured by BASF) was only charged by the same process as in Example 1 without compressed air blow, and the copolymer was fixed on the membrane by applying 25 kGy of γ radiation. The measurement of the ester carbon content was performed twice under the same conditions. The results are shown in the table below. A large amount of VA64 was successfully and uniformly localized at the surface of the functional layer, even when γ radiation was applied to the membrane being immersed in the VA64 solution, and high resistance to the deposition of platelets and high $\beta_2$-microglobulin clearance performance were obtained. This may be because VA64 has a high adsorption equilibrium constant on polysulfone, so that VA64 can adsorb to the surface of the hollow fiber membrane even while the membrane is immersed in the solution.

Example 7

The same process as in Example 1 was performed, except that an aqueous solution of 0.1% by weight of a vinylpyrrolidone/vinyl acetate (7/3) copolymer (Luviskol VA73, manufactured by BASF) was used instead. The measurement of the ester carbon content was performed twice under the same conditions. The results are shown in the table below. A large amount of VA73 was successfully localized at the surface of the functional layer, and high resistance to the deposition of platelets and high $\beta_2$-microglobulin clearance performance were obtained. The resistance to the deposition of platelets was slightly lower in this example than in Example 1. This may be because the ester group content of the functional layer surface is lower in this example than in Example 1, so that the ester group distribution is uneven. The adsorption equilibrium constant of Kollidon VA73 on a polysulfone film is shown in the table.

Example 8

The same process as in Example 1 was performed, except that an aqueous solution of 0.01% by weight of a vinylpyrrolidone/vinyl acetate (7/3) copolymer (Luviskol VA73, manufactured by BASF) was used instead. The results are shown in the table below. A large amount of VA73 was successfully localized at the surface of the functional layer. The deposition of platelets was reduced as compared with Comparative Example 1, but the level of the deposition was rather slightly higher than that in Example 3. This may be because the VA73 molecule has a relatively small number of ester groups and has a worse hydrophilicity-hydrophobicity balance than VA64, so that the resistance to the deposition is lower.

Example 9

Five hundred mL of an aqueous 60% by weight methanol solution of 0.1% by weight of a vinylpyrrolidone/vinyl acetate (3/7) copolymer (Luviskol VA37, manufactured by BASF) was allowed to pass through the hollow fiber membrane module from the blood side inlet to the blood side outlet. Then, 500 mL of the solution was allowed to pass from the blood side inlet to the dialyzate side inlet. Water was further allowed to pass in the same manner for replacement with water in the module. Thereafter, blow and γ radiation were applied as in Example 1. The results are shown in the table below. High separation membrane performance and high resistance to the deposition of platelets were achieved at the same time, even when an aqueous alcohol solution of a vinylpyrrolidone/vinyl acetate (3/7) copolymer, which was insoluble in water, was introduced into the separation membrane and γ radiation was applied after replacement with water. A large amount of VA37 was successfully and uniformly localized at the surface of the functional layer, and high resistance to the deposition of platelets and high $\beta_2$-microglobulin clearance performance were obtained. The adsorption equilibrium constant of Luviskol VA37 on a polysulfone film is shown in the table.

Example 10

An aqueous solution of 0.01% by weight of a vinylpyrrolidone/vinyl acetate (3/7) copolymer (Luviskol VA37, manufactured by BASF) was prepared. The aqueous solution was slightly whitish, but no insoluble matter was visually observed. The same process as in Example 9 was performed using the aqueous solution. The results are shown in the table below. High separation membrane performance and high resistance to the deposition of platelets were achieved at the same time. A large amount of VA37 was successfully and uniformly localized at the surface of the functional layer, and high resistance to the deposition of platelets and high $\beta_2$-microglobulin clearance performance were obtained.

Example 11

The same process as in Example 9 was performed, except that an aqueous 60% by weight methanol solution of 0.01% by weight of polyvinyl acetate was used instead. The measurement of the ester carbon content was performed twice under the same conditions. The results are shown in the table below. Polyvinyl acetate, which was hardly soluble in water, was successfully introduced into the membrane, so that high separation membrane performance and high resistance to the deposition of platelets were achieved at the same time. A large amount of polyvinyl acetate was successfully and uniformly localized at the surface of the functional layer, and high resistance to the deposition of platelets and high $\beta_2$-microglobulin clearance performance were obtained. Since polyvinyl acetate was hardly soluble in water, the adsorption equilibrium constant was not able to be determined.

Example 12

The same process as in Example 1 was performed, except that an aqueous solution of 0.1% by weight of polyvinyl alcohol (PVA) (10,000 in molecular weight, 80% in saponification degree) was used instead. The results are shown in the table below. A large amount of PVA was successfully localized at the surface of the functional layer. The $\beta_2$-microglobulin clearance performance was a slightly low value, but it is apparent that the value is kept higher than that in Comparative Example 7.

Comparative Example 1

The same process as in Example 1 was performed, except that water was used instead. The measurement of the ester carbon content was performed twice under the same conditions. The results are shown in the table below. High $\beta_2$-microglobulin clearance performance was obtained, but platelets were significantly deposited on the surface. The water content of the insoluble component was 94.7%, and the relative rate of adsorption of fibrinogen was 110%.

Comparative Example 2

The same process as in Example 1 was performed, except that an aqueous solution of 0.1% by weight of PVP (K90, manufactured by BASF) was used instead. The measurement of the ester carbon content was performed twice under the same conditions. The results are shown in the table below. High $\beta_2$-microglobulin clearance performance was obtained, but platelets were significantly deposited on the surface. The adsorption equilibrium constant of PVP on a polysulfone film is shown in the table.

Comparative Example 3

The same process as in Example 1 was performed, except that an aqueous solution of 0.1% by weight of polyethylene glycol (6,000 in molecular weight) was used instead. The measurement of the ester carbon content was performed twice under the same conditions. The results are shown in the table below. High $\beta_2$-microglobulin clearance performance was obtained, but platelets were significantly deposited on the surface. The adsorption equilibrium constant of polyethylene glycol on a polysulfone film is shown in the table.

Comparative Example 4

The same process as in Example 1 was performed, except that an aqueous solution of 0.1% by weight of a vinylpyrrolidone/styrene (7/3) copolymer (ANTRA (trademark) 430, manufactured by ISP, Inc.) was used instead. The measurement of the ester carbon content was performed twice under the same conditions. The results are shown in the table below. Platelets were significantly deposited on the surface produced with ANTRA® 430, which was a copolymer comprising a hydrophilic unit and a hydrophobic unit, although it contained no ester group. This may be because styrene is too hydrophobic so that the resistance to the deposition of platelets becomes low.

Comparative Example 5

The same process as in Example 1 was performed, except that an aqueous solution of a mixture of 0.0001% by weight of a vinylpyrrolidone/vinyl acetate (6/4) copolymer (Kollidon VA64 manufactured by BASF) and 0.1% by weight of ethanol was used instead. The results are shown in the table below. VA64 was not able to be localized at the surface of the functional layer, so that resistance to the deposition of platelets was hardly observed. The water content of the insoluble component was 97.1%, and the relative rate of adsorption of fibrinogen was 105%. It is considered that since the ester group content of the inner surface of the hollow fiber membrane was low, the deposition of fibrinogen was not able to be inhibited, although the water content of the insoluble component was at a similar level to that in Example 4.

Comparative Example 6

The same process as in Example 1 was performed, except that 1% by weight of a vinylpyrrolidone/vinyl acetate (6/4) copolymer (Kollidon VA64 manufactured by BASF) was used instead. The results are shown in the table below. The VA64 content of the functional layer surface was too high, so that the $\beta_2$-microglobulin clearance performance was significantly low, although resistance to the deposition of platelets was obtained.

Comparative Example 7

An aqueous solution of 0.1% by weight of PVA (10,000 in molecular weight, 80% in saponification degree) was allowed to pass at a rate of 200 mL/minute for 30 minutes through a single route from the blood side inlet (Bi) of the hollow fiber module to the blood side outlet (Bo) and then from the dialyzate side inlet (Di) to the dialyzate side outlet (Do). Thereafter, blow, replacement with nitrogen, and γ irradiation were performed as in Example 1. The results are shown in the table below. It is considered that since the solution was allowed to equally pass through the inside and the outside of the hollow fiber membrane, a large amount of PVA was also placed in the thickness part of the membrane including pores, so that the $\beta_2$-microglobulin clearance performance was significantly reduced.

Comparative Example 8

Five hundred mL of an aqueous 60% by weight methanol solution of 0.1% by weight of polyvinyl acetate was allowed to pass through the hollow fiber membrane module from the dialyzate side outlet (Do) to the blood side outlet (Bo). Then, 500 mL of the solution was allowed to pass from the blood side inlet (Bi) to the blood side outlet (Bo). Thereafter, the methanol was replaced with pure water by the same process, and then, blow, replacement with nitrogen, and γ irradiation were performed as in Example 1. The results are shown in the table below. A large amount of polyvinyl acetate was allowed to exist on the opposite side from the functional layer, so that the $\beta_2$-microglobulin clearance performance was significantly reduced.

The polysulfone (PSf) hollow fiber membrane (hollow fiber membrane 2) was used in Examples 13 and 14 and Comparative Example 9 described below.

Example 13

Thirty six polysulfone (PSf) hollow fiber membranes (hollow fiber membrane 2) were inserted into a plastic tube, and both ends were fixed with an adhesive, so that a plastic tube mini-module with an effective length of 100 mm was prepared, which was sufficiently washed with pure water. Then, 3 mL of an aqueous solution of 0.01% by weight of a vinylpyrrolidone/vinyl acetate (6/4) copolymer (Kollidon VA64 manufactured by BASF) was allowed to pass through the inside of the hollow fiber membrane, and then 3 mL of the solution was allowed to pass through the hollow fiber membrane from the inside to the outside. Thereafter, the solution on the inside and the outside was removed by a blow, and then 25 kGy of γ radiation was applied. After the γ irradiation, the membrane was sufficiently washed with pure water and subjected to each test.

To examine the performance of the hollow fiber membrane, $\beta_2$-microglobulin clearance was measured by the method described below. Specifically, $\beta_2$-microglobulin was added at a concentration of 5 mg/L to bovine serum at 37° C. The bovine serum was allowed to flow through the blood side of the mini-module at a rate of 1 mL/minute, while a saline solution was allowed to flow through the dialyzate side at a rate of 20 mL/minute at 37° C. After 2 hour circulation, the whole amounts of the bovine serum and the saline solution were collected from the blood side and the dialyzate side, respectively, and the analysis was delegated to SRL, Inc., by which the concentration of $\beta_2$-microglobulin was measured. From the result of the measurement, the clearance was calculated per 1.8 $m^2$.

In the mini-module, the measurement of the $\beta_2$-microglobulin clearance varies from experiment to experiment. Therefore, a control was added in every experiment so that the experiment could be compared. The control used was the hollow fiber membrane of an artificial kidney TORAYSULFONE TS-1.6UL manufactured by TORAY INDUSTRIES, INC. The controls of TS-1.6UL used were from the same production lot. Percentage was used for comparison with the result of the measurement with TS-1.6UL, and the relative clearance rate (%) was calculated and used for comparison between the experiments.

The results are shown in the table below. A large amount of VA64 was successfully and uniformly localized at the surface of the functional layer, and high resistance to the deposition of platelets and high $\beta_2$-microglobulin clearance performance were obtained. The effect of inhibiting the deposition of platelets was slightly lower in this example than in Example 2. This may be because of the presence of PVP, a water-soluble polymer. The adsorption equilibrium constant of Kollidon VA64 on a polysulfone film is the same as that in Example 1.

Example 14

An aqueous 60% by weight methanol solution of 0.01% by weight of polyvinyl acetate was introduced by the same process as in Example 13, and then methanol was replaced with water as described above. Thereafter, blow, replacement with nitrogen, and γ irradiation were performed as in Example 13. The results are shown in the table below. A large amount of polyvinyl acetate was successfully and uniformly localized at the surface of the functional layer, and high resistance to the deposition of platelets and high $β_2$-microglobulin clearance performance were obtained. The effect of inhibiting the deposition of platelets was slightly lower in this example than in Example 11. This may be because of the absence of PVP, a water-soluble polymer. The effect of inhibiting the deposition of platelets was also slightly lower in this example than in Example 13. This may be because of the absence of the vinylpyrrolidone unit in the polyvinyl acetate molecule.

Comparative Example 9

The same process as in Example 13 was performed, except that water was used instead. The results are shown in the table below. Platelets were significantly deposited on the surface.

The chloroacetamidemethylated polysulfone (CAMPS)-containing hollow fiber membrane (hollow fiber membrane 3) was used in Example 15 and Comparative Example 10 below.

Example 15

Thirty six chloroacetamidemethylated polysulfone (CAMPS)-containing hollow fiber membranes were inserted into a plastic tube, and both ends were fixed with an adhesive, so that a plastic tube mini-module with an effective length of 100 mm was prepared, which was sufficiently washed with pure water. The chloroacetamidemethyl group can easily react with an amino group. Therefore, an allylamine/vinyl acetate copolymer was then fixed principally on the functional layer surface of the hollow fiber membrane. Specifically, after water charged into the inside and outside of the hollow fiber membrane was removed, an aqueous 60% by weight isopropanol solution of 5% by weight of an allylamine/vinyl acetate copolymer (the pH was adjusted to 9.0) was allowed to pass through only the inside of the hollow fiber membrane module and allowed to react at room temperature for 1 hour. After the reaction, the unreacted allylamine/vinyl acetate copolymer was washed off with an aqueous 60% by weight isopropanol solution, which was followed by washing and replacement with pure water. The hollow fiber membrane was then subjected to each test.

Concerning the performance of the hollow fiber membrane, $β_2$-microglobulin clearance was measured as in Example 13. The results are shown in the table below. A large amount of VA64 was successfully and uniformly fixed on the surface of the functional layer, and high resistance to the deposition of platelets and high $β_2$-microglobulin clearance performance were obtained. The $β_2$-microglobulin clearance performance was higher in this example than in Comparative Example 10. This may be because the fixation of VA64 on the functional layer surface enhances the effect of inhibiting the deposition of proteins and so on, so that the performance is less reduced by clogging of the membrane with proteins. In this example, chemical fixation rather than coating was performed. Therefore, the adsorption equilibrium of CAPMS on the allylamine/vinyl acetate copolymer was not measured.

Comparative Example 10

Thirty six chloroacetamidemethylated polysulfone-containing hollow fiber membranes were inserted into a plastic tube, and both ends were fixed with an adhesive, so that a plastic tube module with an effective length of 100 mm was prepared, which was sufficiently washed with pure water. An aqueous 60% by weight isopropanol solution (the pH was adjusted to 9.0) was allowed to pass through only the inside of the hollow fiber membrane module and allowed to stand at room temperature for 1 hour. Thereafter, washing and replacement with pure water was performed. The hollow fiber membrane was then subjected to each test. The $β_2$-microglobulin clearance was measured as in Example 11. The results are shown in the table below. Platelets were significantly deposited on the surface, and the $β_2$-microglobulin clearance performance was also lower in this example than in Example 15.

Example 16 and Comparative Example 11 described below were performed for the comparison of the addition of the ester group-containing polymer to the injection liquid (using hollow fiber membrane 4 or 5).

Example 16

Thirty six pieces of hollow fiber membrane 4 were inserted into a plastic tube, and both ends were fixed with an adhesive, so that a plastic tube mini-module with an effective length of 100 mm was prepared, which was sufficiently washed with pure water. Water was removed from the inside and outside of the hollow fiber membrane using a compressed air blow, and then 25 kGy of γ radiation was applied. After the γ irradiation, washing with pure water was sufficiently performed, and each test was performed. Concerning the performance of the hollow fiber membrane, $β_2$-microglobulin clearance was measured as in Example 13. The results are shown in the table below. The deposition of platelets was inhibited, and high $β_2$-microglobulin clearance performance was obtained. The $β_2$-microglobulin clearance performance was higher in this example than in Comparative Example 11. This may be because the coating of the functional layer surface with VA64 enhances the effect of inhibiting the deposition of proteins and so on, so that the performance is less reduced by clogging of the membrane with proteins.

Comparative Example 11

Thirty six pieces of hollow fiber membrane 5 were inserted into a plastic tube, and the same process as in Example 16 was performed. The resulting hollow fiber membrane was also subjected to the same evaluation. The results are shown in the table below. Platelets were significantly deposited on the surface, and the $β_2$-microglobulin clearance performance was lower in this example than in Example 16.

The polyacrylonitrile (PAN) hollow fiber membrane (hollow fiber membrane 6) was used in Example 17 and Comparative Examples 12 and 13 below.

Example 17

Thirty six pieces of hollow fiber membrane 6 were inserted into a plastic tube, and both ends were fixed with an adhesive, so that a plastic tube mini-module with an effective length of 100 mm was prepared, which was sufficiently washed with pure water. After 3 mL of an aqueous solution of 0.1% by weight of a vinylpyrrolidone/vinyl acetate (6/4) copolymer (Kollidon VA64 manufactured by BASF) was allowed to pass through the inside of the hollow fiber membrane, 3 mL of the solution was allowed to pass through the hollow fiber membrane from the inside to the outside. Thereafter, the solution was removed from the inside and the outside, and then 25 kGy of γ radiation was applied. After the γ irradiation, the membrane was sufficiently washed with pure water and subjected to each test. Concerning the performance of the hollow fiber membrane, $\beta_2$-microglobulin clearance was measured as in Example 13. The results are shown in the table below. The deposition of platelets was inhibited, and high $\beta_2$-microglobulin clearance performance was obtained. The $\beta_2$-microglobulin clearance performance was higher in this example than in Comparative Example 12 or 13. This may be because the coating of the functional layer surface with VA64 enhances the effect of inhibiting the deposition of proteins and so on, so that the performance is less reduced by clogging of the membrane with proteins. The adsorption equilibrium constant of Kollidon VA64 on a PAN film is shown in the table.

Comparative Example 12

The same process as in Example 17 was performed, except that 36 pieces of hollow fiber membrane 6 were inserted into a plastic tube and that pure water was used in place of the vinylpyrrolidone/vinyl acetate (6/4) copolymer. The results are shown in the table below. Platelets were significantly deposited on the surface, and the $\beta_2$-microglobulin clearance performance was lower in this example than in Example 17.

Comparative Example 13

The same process as in Example 17 was performed, except that 36 pieces of hollow fiber membrane 6 were inserted into a plastic tube and that an aqueous solution of 0.1% by weight of PVP (K90 manufactured by BASF) was used in place of the vinylpyrrolidone/vinyl acetate (6/4) copolymer. The results are shown in the table below. Platelets were significantly deposited on the surface, and the $\beta_2$-microglobulin clearance performance was lower in this example than in Example 17. The adsorption equilibrium constant of PVP on a PAN film is shown in the table.

TABLE 1

PSf/PVP hollow fiber membrane

| | Process | Ester carbon content (at. %) Inner surface | Ester carbon content (at. %) Outer surface | Vinyl acetate ratio of surface to inside | Aco/Acc Average | Aco/Acc Rate for 0.001 or less | Surface vinyl-pyrrolidone content (wt %) | Number of deposited platelets (/4.3 × 10$^3$ μm$^2$) | $\beta_2$ MG clearance (ml/min) | Equilibrium constant (pg/mm$^2$ppm) |
|---|---|---|---|---|---|---|---|---|---|---|
| Example 1 | (1) VA64 0.1 wt % Bi→Bo (2) VA64 0.1 wt % Bi→Di (3) blow, replacement with nitrogen, γ radiation | 2.4 2.4 | 1.7 1.2 | 289 | 0.110 | 0% | 37 | 2 | 60 | 676 |
| Example 2 | (1) VA64 0.01 wt % Bi→Bo (2) VA64 0.01 wt % Bi→Di (3) blow, replacement with nitrogen, γ radiation | 1.6 1.6 | 1.1 0.61 | 208 | 0.082 | 0% | 34 | 1 | 68 | 676 |
| Example 3 | (1) VA64 0.001 wt % Bi→Bo (2) VA64 0.001 wt % Bi→Di (3) blow, replacement with nitrogen, γ radiation | 0.82 0.82 | 0.59 0 | 2721 | 0.004 | 66% | 30 | 15 | 67 | 676 |
| Example 4 | (1) VA64 0.001 wt % + EtOH0.1 wt % Bi→Bo (2) VA64 0.001 wt % + EtOH0.1 wt % Bi→Di (3) blow, replacement with nitrogen, γ radiation | 0.91 0.91 | 0.65 0 | 1929 | 0.014 | 4.8% | 35 | 1 | 67 | 676 |

TABLE 1-continued

PSf/PVP hollow fiber membrane

| | Process | Ester carbon content (at. %) Inner surface | Ester carbon content (at. %) Outer surface | Vinyl acetate ratio of surface to inside | Aco/Acc Average | Aco/Acc Rate for 0.001 or less | Surface vinyl-pyrrolidone content (wt %) | Number of deposited platelets (/4.3 × 10³ μm²) | $\beta_2$ MG clearance (ml/min) | Equilibrium constant (pg/mm²ppm) |
|---|---|---|---|---|---|---|---|---|---|---|
| Example 5 | (1) VA64 0.0005 wt % + EtOH0.1 wt % Bi→Bo (2) VA64 0.0005 wt % + EtOH0.1 wt % Bi→ | 0.51 | 0 | 600 | 0.010 | 15% | 29 | 8 | 65 | 676 |
| Example 6 | (1) VA64 0.01 wt % Bi→Bo (2) VA64 0.01 wt % Bi→Di (3) γ radiation | 2.2 2.2 | 1.7 1.7 | 853 | 0.049 | 0% | 37 | 1 | 58 | 676 |
| Example 7 | (1) VA73 0.1 wt % Bi→Bo (2) VA73 0.1 wt % Bi→Di (3) blow, replacement with nitrogen, γ radiation | 1.2 1.2 | 0.98 0.51 | 1492 | 0.011 | 12% | 31 | 11 | 67 | 558 |
| Example 8 | (1) VA73 0.01 wt % Bi→Bo (2) VA73 0.01 wt % Bi→Di (3) blow, replacement with nitrogen, γ radiation | 0.79 | 0 | 1568 | 0.007 | 34% | 28 | 38 | 65 | 558 |
| Example 9 | (1) VA37 0.1 wt % Bi→Bo (2) VA37 0.1 wt % Bi→Di (3) blow, replacement with nitrogen, γ radiation | 7.0 | 3.5 | 436 | 0.196 | 0% | 35 | 2 | 57 | 790 |
| Example 10 | (1) VA37 0.01 wt % Bi→Bo (2) VA37 0.01 wt % Bi→Di (3) blow, replacement with nitrogen, γ radiation | 4.4 | 2 | 1301 | 0.075 | 0% | 33 | 2 | 66 | 790 |
| Example 11 | (1) Polyvinyl acetate 0.01 wt % Bi→Bo (2) Polyvinyl acetate 0.01 wt % Bi→Di (3) blow, replacement with nitrogen, γ radiation | 9.7 9.2 | 3.3 2.7 | 2206 | 0.108 | 0% | 20 | 1 | 55 | —[2] |
| Example 12 | (1) PVA 0.1 wt % Bi→Bo (2) PVA 0.1 wt % Bi→Di (3) blow, replacement with nitrogen, γ radiation | 7.9 | 2.8 | 1568 | 0.063 | 0% | 20 | 15 | 48 | 1183 |

[1] ATR was not measured, because the ester carbon content of the inner surface was not higher than the detection limit.
[2] It was not measured, because polyvinyl acetate was hardly soluble in water.
[3] It was not measured because of the absence of polymer.
For the ester carbon content, 0 indicates the detection limit or less.

TABLE 2

| | | Ester carbon content (at. %) | | Vinyl acetate ratio of | Aco/Acc | | Surface vinyl-pyrrolidone | Number of deposited | $\beta_2$ MG | Equilibrium |
|---|---|---|---|---|---|---|---|---|---|---|
| | Process | Inner surface | Outer surface | surface to inside | Average | Rate for 0.001 or less | content (wt %) | platelets (/4.3 × 10³ μm²) | clearance (ml/min) | constant (pg/mm²ppm) |
| Comparative Example 1 | (1) Water Bi→Bo (2) Water Bi→Di (3) blow, replacement with nitrogen, γ radiation | 0 0 | 0 0 | —¹⁾ | —¹⁾ | —¹⁾ | 20 | >100 | 65 | —³⁾ |
| Comparative Example 2 | (1) PVP 0.1 wt % Bi→Bo (2) PVP 0.1 wt % Bi→Di (3) blow, replacement with nitrogen, γ radiation | 0 0 | 0 0 | —¹⁾ | —¹⁾ | —¹⁾ | 21 | >100 | 65 | 310 |
| Comparative Example 3 | (1) PEG 0.1 wt % Bi→Bo (2) PEG 0.1 wt % Bi→Di (3) blow, replacement with nitrogen, γ radiation | 0 0 | 0 0 | —¹⁾ | —¹⁾ | —¹⁾ | 19 | >100 | 65 | 270 |
| Comparative Example 4 | (1) ANTRA 430 0.1 wt % Bi→Bo (2) ANTRA 430 0.1 wt % Bi→Di (3) blow, replacement with nitrogen, γ radiation | 0 0 | 0 0 | —¹⁾ | —¹⁾ | —¹⁾ | 27 | 68 | 59 | 320.00 |
| Comparative Example 5 | (1) VA64 0.0001 wt % + EtOH0.1 wt % Bi→Bo (2) VA64 0.0001 wt % + EtOH0.1 wt % Bi→ | 0 | 0 | —¹⁾ | —¹⁾ | —¹⁾ | 22 | >100 | 65 | 676 |
| Comparative Example 6 | (1) VA64 1 wt % Bi→Bo (2) VA64 1 wt % Bi→Di (3) blow, replacement with nitrogen, γ radiation | 11 | 5 | 789 | 0.350 | 0% | 41 | 2 | 38 | 676 |
| Comparative Example | (1) PVA 0.1 wt % Bi→Bo→Di→Do (3) blow, replacement with nitrogen, γ radiation | 10.5 | 8.5 | 6975 | 0.044 | 0% | 20 | 2 | 29 | 1183 |

TABLE 2-continued

PSf/PVP hollow fiber membrane

| | Process | Ester carbon content (at. %) Inner surface | Ester carbon content (at. %) Outer surface | Vinyl acetate ratio of surface to inside | Aco/Acc Average | Aco/Acc Rate for 0.001 or less | Surface vinyl-pyrrolidone content (wt %) | Number of deposited platelets (/4.3 × 10³ μm²) | $\beta_2$ MG clearance (ml/min) | Equilibrium constant (pg/mm²ppm) |
|---|---|---|---|---|---|---|---|---|---|---|
| Comparative Example 8 | (1) Polyvinyl acetate 0.1 wt % Do→Bo (1) Polyvinyl acetate 0.1 wt % Bi→Bo (3) blow, replacement with nitrogen, γ radiation | 9.7 | 11 | 784 | 0.330 | 0% | 20 | 3 | 17 | —[2)] |

[1)] ATR was not measured, because the ester carbon content of the inner surface was not higher than the detection limit.
[2)] It was not measured, because polyvinyl acetate was hardly soluble in water.
[3)] It was not measured because of the absence of polymer.
For the ester carbon content, 0 indicates the detection limit or less.

TABLE 3

PSf hollow fiber membrane

| | Process | Ester carbon content (at. %) Inner surface | Ester carbon content (at. %) Outer surface | Vinyl acetate ratio of surface to inside | Aco/Acc Average | Aco/Acc Rate for 0.001 or less | Surface vinyl-pyrrolidone content (wt %) | Number of deposited platelets (/4.3 × 10³ μm²) | $\beta_2$ MG clearance (ml/min) | Equilibrium constant (pg/mm²ppm) |
|---|---|---|---|---|---|---|---|---|---|---|
| Example 13 | (1) VA64 0.01 wt % (passing through only the inside of the membrane) (2) VA64 0.01 wt % (passing from the inside to the outside of the membrane) (3) blow, replacement with nitrogen, γ radiation | 0.81 | 0 | 289 | 0.053 | 1.5% | 15 | 5 | 62 | 676 |
| Example 14 | (1) Polyvinyl acetate 0.01 wt % (passing through only the inside of the membrane) (2) Polyvinyl acetate 0.01 wt % (passing from the inside to the outside of the membrane) (3) blow, replacement with nitrogen, γ radiation | 9.7 | 2.7 | 252 | 0.707 | 0% | 0 | 19 | 60 | —[2)] |
| Comparative Example 9 | (1) Water (passing through only the inside of the membrane) (2) Water (passing from the inside to the outside of the | 0 | 0 | —[1)] | —[1)] | —[1)] | 0 | >100 | 59 | —[3)] |

TABLE 3-continued

PSf hollow fiber membrane

| Process | Ester carbon content (at. %) Inner surface | Ester carbon content (at. %) Outer surface | Vinyl acetate ratio of surface to inside | Aco/Acc Average | Aco/Acc Rate for 0.001 or less | Surface vinyl-pyrrolidone content (wt %) | Number of deposited platelets (/4.3 × 10³ μm²) | $\beta_2$ MG clearance (ml/min) | Equilibrium constant (pg/mm²ppm) |
|---|---|---|---|---|---|---|---|---|---|
| membrane) (3) blow, replacement with nitrogen, γ radiation | | | | | | | | | |

[1] ATR was not measured, because the ester carbon content of the inner surface was not higher than the detection limit.
[2] It was not measured, because polyvinyl acetate was hardly soluble in water.
[3] It was not measured because of the absence of polymer.
For the ester carbon content, 0 indicates the detection limit or less.

TABLE 4

CAPMS hollow fiber membrane

| | Reaction solution | Ester carbon content (at. %) Inner surface | Ester carbon content (at. %) Outer surface | Vinyl acetate ratio of surface to inside | Aco/Acc Average | Aco/Acc Rate for 0.001 or less | Surface vinylpyrrolidone content (wt %) | Number of deposited platelets (/4.3 × 10³ μm²) | $\beta_2$ MG clearance (ml/min) | Equilibrium constant (pg/mm²ppm) |
|---|---|---|---|---|---|---|---|---|---|---|
| Example | Allylamine/vinyl acetate copolymer | 1.4 | 0 | 263 | 0.075 | 0% | 25 | 7 | 51 | —[4] |
| Comparative Example | Water | 0 | 0 | —[1] | —[1] | —[1] | 25 | >100 | 48 | —[4] |

[1] ATR was not measured, because the ester carbon content of the inner surface was not higher than the detection limit.
[4] The adsorption equilibrium was not measured, because polymer adsorption was not performed.
For the ester carbon content, 0 indicates the detection limit or less.

TABLE 5

Experiment of addition to injection liquid

| | Injection liquid composition | Ester carbon content (at. %) Inner surface | Ester carbon content (at. %) Outer surface | Vinyl acetate ratio of surface to inside** | Aco/Acc Average | Aco/Acc Rate for 0.001 or less | Surface vinylpyrrolidone content (wt %) | Number of deposited platelets (/4.3 × 10³ μm²) | $\beta_2$ MG clearance (ml/min) | Equilibrium constant (pg/mm²ppm) |
|---|---|---|---|---|---|---|---|---|---|---|
| Example | VA64 10 wt % dissolved in DMAc/water (63/37) solution | 1.3 | 0 | 278 | 0.072 | 0% | 33 | 7 | 51 | —[4] |
| Comparative Example | DMAc/water (63/37) solution | 0 | 0 | —[1] | —[1] | —[1] | 25 | >100 | 48 | —[4] |

[1] ATR was not measured, because the ester carbon content of the inner surface was not higher than the detection limit.
[4] The adsorption equilibrium was not measured, because polymer adsorption was not performed.
For the ester carbon content, 0 indicates the detection limit or less.

TABLE 6

PAN hollow fiber membrane

| | Process | Ester carbon content (at. %) Inner surface | Ester carbon content (at. %) Outer surface | Vinyl acetate ratio of surface to inside | Aco/Acc Average | Aco/Acc Rate for 0.001 or less | Surface vinyl-pyrrolidone content (wt %) | Number of deposited platelets (/4.3 × 10³ μm²) | $\beta_2$ MG clearance (ml/min) | Equilibrium constant (pg/mm²ppm) |
|---|---|---|---|---|---|---|---|---|---|---|
| Example 17 | (1) VA64 0.1 wt % (passing through only the inside of the membrane) (2) VA64 0.1 wt % (passing from the inside to the outside of the membrane) (3) blow, replacement with nitrogen, γ radiation | 0.9 | 0 | 56 | 0.08 | 0% | 15 | 5 | 25 | 420 |
| Comparative Example 12 | (1) Water (passing through only the inside of the membrane) (2) Water (passing from the inside to the outside of the membrane) (3) blow, replacement with nitrogen, γ radiation | 0 | 0 | —¹⁾ | —¹⁾ | —¹⁾ | 0 | 60 | 23 | —⁴⁾ |
| Comparative Example 13 | (1) PVP 0.1 wt %(passing through only the inside of the membrane) (2) PVP 0.1 wt %(passing from the inside to the outside of the membrane) (3) blow, replacement with nitrogen, γ radiation | 0 | 0 | —¹⁾ | —¹⁾ | —¹⁾ | 25 | 52 | 24 | 220 |

¹⁾ATR was not measured, because the ester carbon content of the inner surface was not higher than the detection limit.
⁴⁾The adsorption equilibrium was not measured, because polymer adsorption was not performed.
For the ester carbon content, 0 indicates the detection limit or less.

What is claimed:

1. A separation membrane, comprising a membrane comprising a polymer, wherein
the membrane, has a functional layer in one side surface,
the functional layer has a surface showing an ester carbon peak area percentage of 0.1 (at. %) to 10 (at. %) as measured by X-ray electron spectroscopy (ESCA),
the membrane has an opposite surface from the functional layer,
the opposite surface shows an ester carbon peak area percentage of less than 10 (at. %) as measured by X-ray electron spectroscopy (ESCA), a surface of a functional layer has an ester carbon content 10% or more higher than that of an opposite surface from the functional layer,
wherein the separation membrane contains a water-soluble polymer which is polyvinylpyrrolidone, polyethylene glycol, or polyvinyl alcohol, and
wherein the separation membrane contains an insoluble component which remains after the polymer of the separation membrane is dissolved in a good solvent, wherein said insoluble component has a water content of 95% or more.

2. The separation membrane according to claim 1, wherein the ester in the surface of the functional layer is derived from an ester group-containing polymer.

3. The separation membrane according to claim 2, wherein the ester group-containing polymer comprises at least one selected from a vinyl carboxylate ester unit, an acrylate ester unit and a methacrylate ester unit.

4. The separation membrane according to claim 2, wherein the ester group-containing polymer is polyvinyl acetate or a copolymer of vinyl acetate and vinylpyrrolidone.

5. The separation membrane according to claim 1, wherein the membrane comprises a hydrophobic polymer.

6. The separation membrane according to claim 5, wherein the hydrophobic polymer is a polysulfone-based polymer.

7. The separation membrane according to claim 1, wherein the membrane is a hollow fiber membrane.

8. The separation membrane according to claim 1, wherein the membrane is for use in blood purification.

9. A separation membrane module, comprising the separation membrane according to claim 1 as a built-in element.

10. A method of producing a separation membrane comprising a hydrophobic polymer, wherein a surface of a functional layer has an ester carbon content 10% or more higher than that of an opposite surface from the functional layer, wherein the separation membrane contains a water-soluble polymer which is polyvinylpyrrolidone, polyethylene glycol, or polyvinyl alcohol, wherein the separation membrane contains an insoluble component, which remains after the polymer of the separation membrane is dissolved in a good solvent, wherein said insoluble content has a water content of 95% or more, comprising;

forming a coating of an ester group-containing polymer, wherein the ester group-containing polymer has an adsorption equilibrium constant of 330 pg/(mm$^2$·ppm) to 1,100 pg/(mm$^2$·ppm) on the hydrophobic polymer, and a solution of the ester group-containing polymer is brought into contact with the hydrophobic polymer under a pressure difference generated between the inside and the outside of the separation membrane.

11. The method according to claim 10, wherein the step of forming the coating comprises bringing the solution of the ester group-containing polymer into contact with the separation membrane and performing irradiation with radiation and/or heat treatment.

* * * * *